US012292427B2

(12) United States Patent
Caicedo Panqueva et al.

(10) Patent No.: US 12,292,427 B2
(45) Date of Patent: May 6, 2025

(54) GAS SENSOR DEVICE WITH HIGH SENSITIVITY AT LOW TEMPERATURE AND METHOD OF FABRICATION THEREOF

(71) Applicant: LUXEMBOURG INSTITUTE OF SCIENCE AND TECHNOLOGY (LIST), Esch-sur-Alzette (LU)

(72) Inventors: Nohora Caicedo Panqueva, Esch-sur-Alzette (LU); Damien Lenoble, Wellin (BE); Renaud Leturcq, Luxembourg (LU); Jean-Sébastien Thomann, Gorcy (FR)

(73) Assignee: LUXEMBOURG INSTITUTE OF SCIENCE AND TECHNOLOGY (LIST), Esch-sur-Alzette (LU)

( * ) Notice: Subject to any disclaimer, the term of this patent is extended or adjusted under 35 U.S.C. 154(b) by 472 days.

(21) Appl. No.: 16/645,579

(22) PCT Filed: Sep. 19, 2018

(86) PCT No.: PCT/EP2018/075370
§ 371 (c)(1),
(2) Date: Mar. 9, 2020

(87) PCT Pub. No.: WO2019/057786
PCT Pub. Date: Mar. 28, 2019

(65) Prior Publication Data
US 2020/0300825 A1     Sep. 24, 2020

(30) Foreign Application Priority Data
Sep. 19, 2017   (LU) .......................................... 100442

(51) Int. Cl.
*G01N 27/12*     (2006.01)
*G01N 27/403*   (2006.01)
*G01N 33/00*     (2006.01)

(52) U.S. Cl.
CPC ......... *G01N 33/004* (2013.01); *G01N 27/127* (2013.01); *G01N 27/403* (2013.01)

(58) Field of Classification Search
CPC ... G01N 33/004; G01N 27/127; G01N 27/403
See application file for complete search history.

(56) References Cited

U.S. PATENT DOCUMENTS

| 8,443,647 B1* | 5/2013 | Kolmakov | ............. B82Y 15/00 73/1.02 |
| 2006/0102494 A1* | 5/2006 | Chueh | ................ G01N 33/0037 205/785.5 |

(Continued)

OTHER PUBLICATIONS

Caicedo et al., Aspect ratio improvement of ZnO nanowires grown in liquid phase by using step-by-step sequential growth, CrystEngComm, vol. 18, Issue 29, pp. 5502-5511 (2016) (Year: 2016).*

(Continued)

*Primary Examiner* — Brian W Cohen
*Assistant Examiner* — Vivian A Tran
(74) *Attorney, Agent, or Firm* — Sandberg Phoenix & von Gontard, P.C.

(57) ABSTRACT

A method for producing a gas sensor comprising a step of providing a substrate with two coplanar electrodes and a step of forming a ZnO nanowires network on the two electrode. The step of forming a ZnO nanowires network on the two electrodes is performed as follows: synthesizing ZnO nanowires with a liquid phase sequential growth method; dispersing the synthetized nanowires in a solvent; drop casting the solution containing the solvent and the ZnO nanowires on the electrodes; drying the solution at a temperature inferior to 85° C. Also, a gas sensor working at low temperature such as room temperature.

5 Claims, 16 Drawing Sheets

(56) References Cited

U.S. PATENT DOCUMENTS

2008/0006078 A1* 1/2008 Chueh .................. G01N 27/127
73/31.06
2010/0089772 A1* 4/2010 Deshusses ........... G01N 27/127
977/773

OTHER PUBLICATIONS

Qi et al., Properties of humidity sensing ZnO nanorods-base sensor fabricated by screen-printing, Sensors and Actuators B: Chemical, vol. 133, Issue 2, pp. 638-643 (2008) (Year: 2008).*
Acuautla Meneses, Development of ozone and ammonia gas sensors on flexible substrates, Thesis, Aix-Marseille University (2014) (Year: 2014).*
International Search Report for corresponding PCT/EP2018/075370 mailed Sep. 1, 2019.

* cited by examiner

|  | $N_2$ -100% | 2% $O_2$ | 5% $O_2$ | 10% $O_2$ | 20% $O_2$ |
|---|---|---|---|---|---|
| $V_1(V) = \dfrac{\eta_1 N_{1,GB} K_B T}{q}$ | 1.92 ± 0.05 | 1.92 ± 0.05 | 1.82 ± 0.06 | 2.00 ± 0.07 | 1.7 ± 0.4 |
| $V_2(V) = \dfrac{\eta_2 N_{2,GB} K_B T}{q}$ | 1.89 ± 0.05 | 1.82 ± 0.05 | 1.99 ± 0.06 | 2.03 ± 0.06 | 1.6 ± 0.3 |
| $R_s (Ohms)$ | 26525 ± 990 | 45294 ± 1770 | 52271 ± 2670 | 74259 ± 5578 | 142909 ± 42093 |
| $I_1 (A)$ | 2.06E-6 ± 1.5E-7 | 1.18E-6 ± 8.7E-8 | 6.39E-7 ± 6.2E-8 | 4.01E-7 ± 3.9E-8 | 1.92E-7 ± 1.3E-7 |
| $I_2 (A)$ | 2.15E-6 ± 1.6E-7 | 9.52E-7 ± 7.9E-8 | 7.72E-7 ± 6.3E-8 | 3.46E-7 ± 3.2E-8 | 1.40E-7 ± 9.6E-8 |

GAS SENSOR DEVICE WITH HIGH SENSITIVITY AT LOW TEMPERATURE AND METHOD OF FABRICATION THEREOF

The present invention is the US national stage under 35 U.S.C. § 371 of International Application No. PCT/EP2018/075370, which was filed on Sep. 19, 2018, and which claims the priority of application LU 100442 filed on Sep. 19, 2017, the content of which (text, drawings and claims) are incorporated here by reference in its entirety.

FIELD

The invention is directed to gas sensors more particularly to metal oxide gas sensors.

BACKGROUND

Metal Oxide (MOx) gas sensors are frequently commercially used in gas sensors due to their high sensitivity. Gas sensors working at room temperature are usually not sensitive enough for proper use. Indeed, the usual sensing principle of MOx gas sensors relies on redox reaction and consequently the gas sensors need to be activated by high temperature, often by temperature above 100° C. in order to provide sufficient high sensitivity.

Thus, there is a need to provide gas sensors providing a high sensitivity to gas at room temperature, without the need of a heater, and to provide a low energy method for fabricating such gas sensors, without annealing.

Prior art patent document published US 2006/0102494 A1 discloses a gas sensor. The gas sensor comprises two separate metal electrodes on a substrate and a semiconductor thin film deposited on the substrate and connecting the two metal electrodes. The semiconductor thin film is made of zinc oxide or zinc oxide mixed with indium in the form of nanowires. The nanowires are synthetized by direct vapour-phase synthesis on the two predefined electrodes at high temperature, above 500° C. The method for fabricating the gas sensor implies very high temperature.

Prior art patent document published U.S. Pat. No. 8,443,647 B1 discloses a sensor device for detecting gas for example. The sensor comprises two electrodes connected by means of nanowires mat. The nanowires are in metal oxide and are grown by a vapor method at 1280 K. There is no disclosure of a gas sensor with a high sensitivity at low temperature, such as room temperature.

Prior art document published GB 2 527 340 A discloses a method for producing a gas sensor at low temperature and a power economic method to produce the gas sensor. The method comprises a step of providing a solution of commercial nanowires in a solvent and placing the solution on a set of at least two electrodes. An AC voltage is then applied on the electrodes in order to provide order in the arrangement of the nanowires. The method of fabrication of the gas sensor implies a dielectrophoretic step. However, sensitivity of the gas sensor at room temperature is obtained by exposing the gas sensor to UV light Prior art document published GB 2 495 074 A discloses a method for producing ZnO nanowires at high temperature by annealing (between 110 and 1000° C.). The nanowires are used to produce a gas sensor. The gas sensor was tested at a temperature over 400° C. The method for synthesizing nanoparticles of ZnO implies very high temperature and the gas sensor show sensitivity only at high temperature.

Prior art document published WO 2008/153593 A discloses a gas sensor comprising two separated electrodes and a functionalised nanomaterial bridging the gap between the electrodes. The nanomaterial can be ZnO nanostructures. A suspension of nanomaterial is deposited on the electrodes in order to form a nanostructure network. The nanostructure network is functionalized by electrodepositing metal oxide nanoparticles on the nanomaterial network in order to form a nano-sensor chip and annealing is performed at high temperature. The method of production of the gas sensor requires high temperature and the document does not disclose gas sensor working at low temperature.

Caicedo. N et al., *CrystEngComm*, 2016, 18, 5502-5551. discloses a method for synthetizing ZnO nanowires however there is no disclosure of a gas sensor working at low temperature and no disclosure of a method for fabrication such gas sensor.

SUMMARY OF INVENTION

The invention has for technical problem to solve at least one drawback of the mentioned prior art. More particularly, the invention has for technical problem to provide a gas sensor with high sensitivity at low temperature, as at room temperature, without the need of additional heating system. The invention has also for technical problem to provide a simple and low-cost method for fabricating such a gas sensor.

The invention is directed to a method for producing a gas sensor comprising a step of providing a substrate with two coplanar electrodes and a step of forming a ZnO nanowires network on the two electrodes, wherein the step of forming a ZnO nanowires network on the two electrodes is performed as follows: a) synthesizing ZnO nanowires with a liquid phase sequential growth method; b) dispersing the synthetized nanowires in a solvent; c) drop casting the solution containing the solvent and the ZnO nanowires on the electrodes; d) drying the solution at a temperature inferior to 85° C.

According to an exemplary embodiment, step a of synthesizing ZnO nanowires comprises the subsequently sub-steps of: a) preparing a solution of zinc chloride and hexamethylenetetramine dissolved into water, wherein zinc chloride and hexamethylenetetramine are equimolar; b) heating the solution at a temperature comprised between 70° and 90° C., in various instances, 85° C.; c) adding every 100 min, equimolar amounts of zinc chloride and hexamethylenetetramine into the solution while keeping heating.

According to an exemplary embodiment, step a) of synthesizing ZnO nanowires is performed under stirring, in various instances, at 350 rpm.

According to an exemplary embodiment, sub-step c) is repeated at least one time, in various instances, two times.

According to an exemplary embodiment, step c) of drop casting comprises depositing a droplet of 50 µL of the ZnO nanowires solution on the electrodes.

According to an exemplary embodiment, steps c) of drop casting and d) of drying are repeated together at least one time, in various instances, two times.

In various embodiments, the invention is also directed to a gas sensor comprising a substrate, two electrodes on the substrate, a ZnO nanowires network on the two electrodes, wherein the ZnO nanowires of the ZnO nanowires network have on their surface HMTA, $NH_3$ and/or $NH_x$.

According to an exemplary embodiment, the electrodes are in metal, in various instances, in gold.

According to an exemplary embodiment, each ZnO nanowire has a length superior to 0.5 µm and/or inferior to 20 µm, in various instances, equals to 3 µm and a diameter superior to 20 nm and/or inferior to 500 nm, in various instances, equals to 250 nm.

According to an exemplary embodiment, each electrode has a thickness superior to 10 nm and/or inferior to 200 nm, in various instances, equal to 50 nm.

According to an exemplary embodiment, each electrode has a length comprised between 2 µm and 5000 µm, in various instances, comprised between 1000 µm and 1100 µm, for example equals to 1050 µm.

According to an exemplary embodiment, the electrodes are interdigitated.

According to an exemplary embodiment, the interdigitated electrodes have interdigitated fingers, the fingers being spaced with each other with a gap comprised 2 and 100 µm, in various instances, equals to 20 µm.

The invention is also directed to a use of a gas sensor to detect $O_2$ and/or $CO_2$ wherein the gas sensor is according to the invention.

According to an exemplary embodiment, the detection is carry on at a temperature comprised between 0° and 100° C.

In the following description, the word "device" refers to the gas sensor of the invention.

The invention is particularly interesting in that the gas sensor of the invention shows high sensitivity to gas at low temperature such as room temperature. The gas sensor of the invention does not need to be activated with high temperature and thus is autonomous. The invention is thus economic in energy. The method of fabrication of the gas sensor according to the invention, does not need any thermal energy and is thus economic. The method of fabrication of the gas sensor according to the invention is also simple to be performed.

DRAWINGS

DETAILED DESCRIPTION

Figure 1:
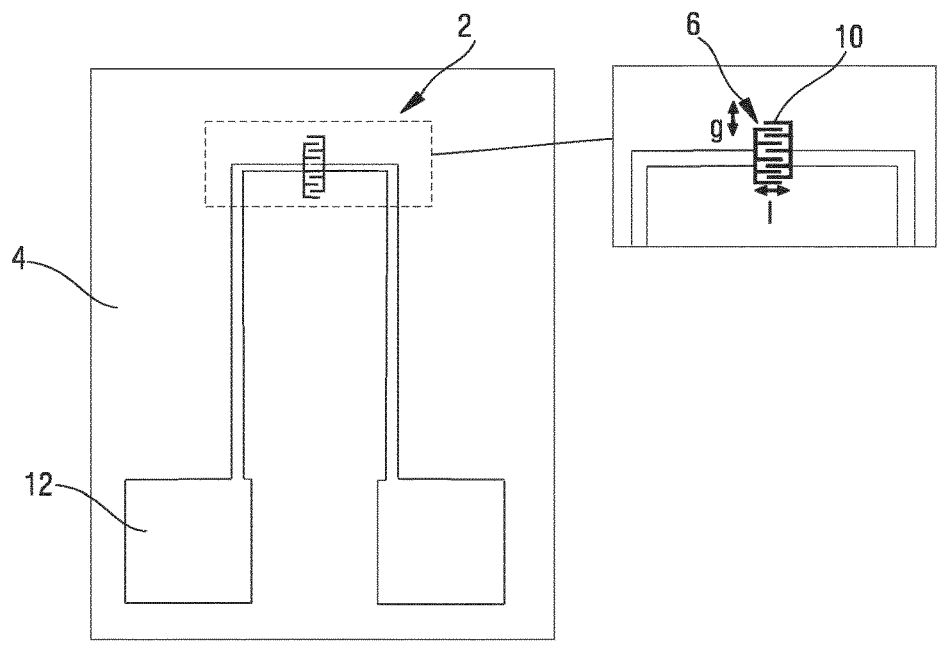
FIG. 1 illustrates a top view of the gas sensor according to various embodiments of the invention.
Figure 2:
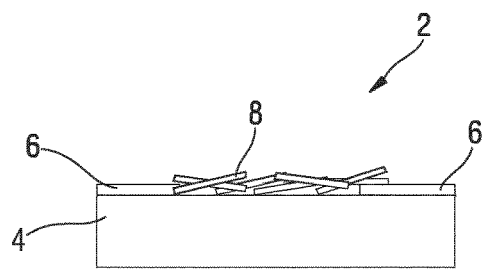
FIG. 2 is a schematic cross section of the gas sensor of the invention illustrated in FIG. 1, according to various embodiments of the invention.

FIGS. 1 and 2 respectively illustrates a top view and a cross section of a gas sensor 2 according to the invention. The gas sensor is fabricating by providing a substrate with two coplanar electrodes and forming a ZnO nanowires network on the two electrodes.

The gas sensor 2 of the invention comprises a substrate 4 on which are deposited two coplanar electrodes 6. The two electrodes 6 are separated. The gas sensor 4 comprises a network 8 of ZnO nanowires connecting the two electrodes. The ZnO nanowires network is only represented on FIG. 2.

Any substrate can be used. The substrate is, in various instances, in silicone and comprises an insulating layer of $SiO_2$ in contact with the electrodes.

The electrodes 6 are in metal, in various instances, in gold. According to an exemplary embodiment of the invention, the two electrodes are interdigitated. The electrodes 6 comprise fingers or digits or probes 10 which are interdigitated. Each finger 10 has a length/superior to 5 µm and/or inferior to 5000 µm, in various instances, comprised between 1000 µm and 1100 µm, more, in various instances, the length of each finger is of 1050 µm. The fingers 10 are separated from each other with a gap g superior to 2 µm and/or inferior to 100 µm, in various instances, comprised between 15 µm and 25 µm, for example the gap is of 20 µm.

The electrodes 6 can be deposited with an electron beam metal evaporator reactor. The interdigitated electrodes are obtained by a lift-off process. The lift-off process can be performed in acetone under sonication. An adhesion layer can be used to deposit the electrodes such as a layer of titanium. The adhesion layer can have a thickness superior to 3 nm and/or inferior to 8 nm, in various instances, equals to 5 nm. The electrodes have, in various instances, a thickness inferior to 200 nm, in various instances, equals to 50 mm.

Each ZnO nanowires of the network has a length superior to 0.5 µm and/or inferior to 20 µm, in various instances, equals to 3 µm and/or a diameter superior to 20 nm and/or inferior to 500 nm, in various instances, equal to 250 nm.

The two electrodes 6 are connected to two electric pads 12, respectively. The two pads can ben squared pad having side length of 3 mm.

The formation of the ZnO nanowires network comprises a step a) of synthesizing ZnO nanowires by a liquid phase sequential growth method. Zinc chloride ($ZnCl_2$) and Hexamethylenetetramine ($C_6H_{12}N_4$-HMTA) are used as precursors. The precursors are prepared as two separate solutions of 1M (mol/L).

Synthesizing ZnO nanowires comprises a first sub-step a) of preparing a solution of zinc chloride and hexamethylenetetramine dissolved into water, wherein zinc chloride and hexamethylenetetramine are equimolar. More particularly a 100 mL solution of 10 mM of zinc chloride into water and a 100 mL solution of 10 mM of hexamethylenetetramine into water have been prepared. The two solutions are respectively prepared by mixing 1M of Zinc chloride and 1M of Hexamethylenetetramine (from Sigma Aldrich) with 100 mL of water more particularly in MilliQ water (18.2 MW cm), in separate containers in order to have each solution at 10 mM. The two solutions are then dissolved into water in order to have one solution. The solution is heated at a temperature comprised between 70° and 90° C., in various instances, 85° C. (sub-step b)). In order to cycle the synthetized of nanowires, step a) of synthesizing ZnO nanowires comprises a sub-step c) of adding every 100 min, equimolar amounts of zinc chloride and hexamethylenetetramine into the solution while keeping heating. The molarity of each amounts is in various instances, the same as in sub-step a). More particularly, 1 mL of Hexamethylenetetramine at 10 mM and 1 mL of Zinc chloride at 10 mM is adding in the solution every 100 min, while keeping heating the solution. Sub-step c) can comprise the addition of PEG (Polyethylene glycol). PEG is, in various instances, added at a concentration inferior to 5%, for example equals to 2%. The sub-step c) is repeated at least one time, in various instances, two times. Advantageously, sub-step c) is repeated twice. The synthesis has been performed under magnetic stirring, in various instances, at 350 rpm and under argon condition.

After the synthesizing step, the method comprises a step b) of dispersing the ZnO nanowires in a solvent, in various instances, in water. The ZnO nanowires can also be dispersed in alcohol, as ethanol for example.

A step c) of drop-casting is then performed on the separated electrodes in order to bridge the gap between the two electrodes. The step of drop-casting comprises depositing, on the two electrodes, a droplet of 50 µL of the solution containing the solvent and the ZnO nanowires. After drop-casting, the solution is then dried at a temperature inferior to 85° C. in a step d). Advantageously, the solution is dried at room temperature (20-30° C.) by evaporation. Step c) of drop casting and step d) of drying are repeated together at least one time, in various instances, two times. Drop casting three droplets of solution on the electrodes allow the formation of a ZnO nanowires network-based thin film with junction between the nanowires. The method of deposition of the nanowires avoid formation of agglomerates in the ZnO nanowires network.

These method for fabricating a gas sensor is simple and does not require high temperature.

Thermal annealing of ZnO nanowires network obtained with the method previously described has been performed under different conditions (Air, Ar, $H_2N_2$ annealing)

Air Annealed ZnO Nanowires

Figure 3:
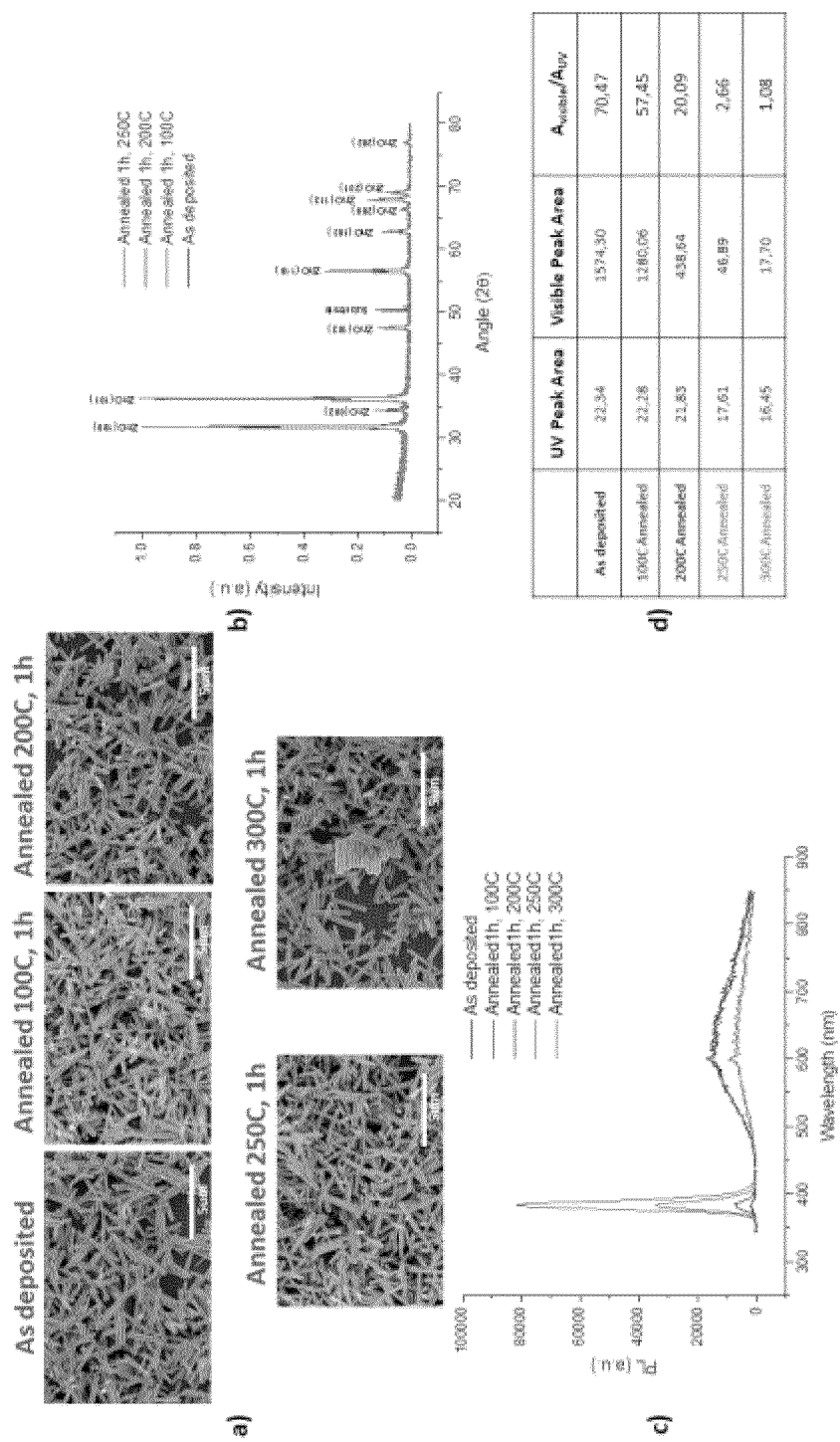
FIG. 3 shows characteristics of Air annealed ZnO nanowires, according to various embodiments of the invention.

The results are reported in FIG. 3. FIG. 3a shows the morphology and crystalline characterization of samples annealed under environmental conditions (Air) at different temperatures during one-hour time. FIG. 3a shows the SEM images of ZnO nanowires for as-grown nanowires, annealed 1 h at 100° C., 200° C., 250° C. and 300° C. The increasing of the annealing temperature is with the purpose of conductivity improvement, when an improvement is no longer observed for air, the temperature is no longer studied. In the case of air, an improvement was observed up to 250° C. annealing afterwards, the conductivity was no further enhanced. From the SEM pictures, no change in the morphology is observed at 100° C., 200° C. and 250° C. as compared to the non-annealed sample (as deposited), when the temperature is increased further than 250° C. under air conditions, some nanowires are found to be pealing, the ZnO surface is detaching from the nanowire itself. FIG. 3b shows the normalized XRD analysis of the samples under different temperatures, from where the wurtzite structure of ZnO is preserved after annealing, the spectra indicates there is no preferred orientation. This XRD pattern is the result of an average signal collected from several random-oriented nanowires thin film with respect to each other and especially to the incident X-ray beam. FIGS. 3c and 3d show a normalized photoluminescent (PL) spectra regarding the UV peak in order to compare visible light photoluminescence behaviour when annealing the samples. Their area ratio for visible peak over UV peak is then calculated for analysis. The ZnO PL spectra shows a dominant orange emission centred at 610 nm, and a weak UV emission at 380 nm was observed upon excited by light with a wavelength of 300 nm for as deposited sample. When the sample is annealed this UV emission is then increased, therefore the ratio in FIG. 3d from the two peaks always decreases with air annealing. Previous studies on ZnO reported a luminescence green peak at 520 nm, which has been attributed to defects associated with oxygen deficiency. Orange emission is due to interstitial oxygen ions.

Ar Annealed ZnO Nanowires

Figure 4:
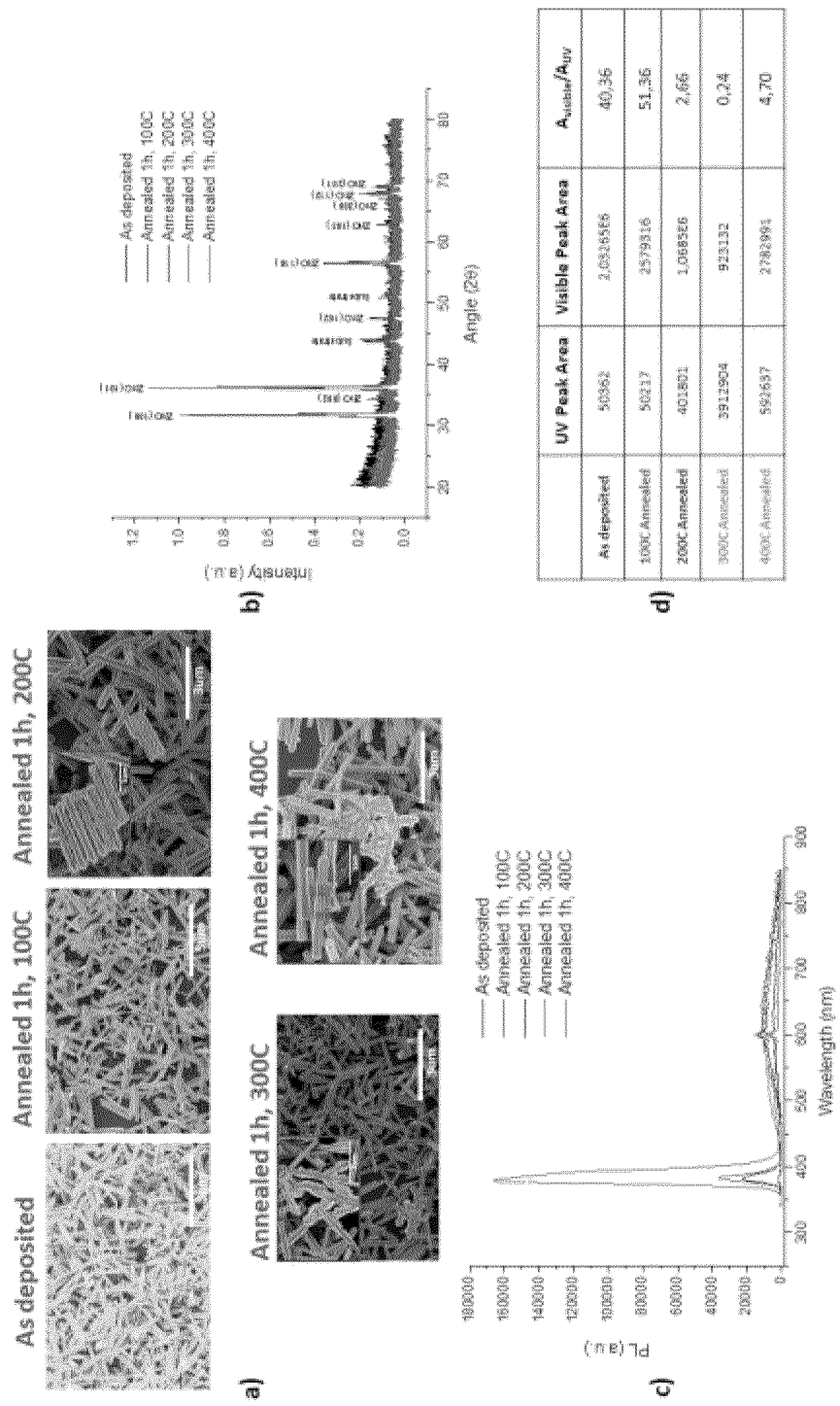
FIG. 4 shows characteristics of Ar annealed ZnO nanowires, according to various embodiments of the invention.

Samples were annealed under a constant Argon flow during one hour for different temperature. The results are reported in FIG. 4. FIG. 4a shows the SEM images of ZnO nanowires for as-grown nanowires, annealed 1 h at 100° C., 200° C., 300° C. and 400° C. The increasing of the annealing temperature is with the purpose of conductivity improvement, when an improvement is no longer observed for Ar, the temperature is no longer studied. In the case of Ar, an improvement was observed up to 300° C. annealing afterwards, the conductivity was no further enhanced. From the SEM pictures, no change is observed at 100° C. as compared to the non-treated sample, when the temperature is increased further than 100° C. under Ar the peeling behavior already discussed and seen for annealed samples under air was again observed, confirming that the peeling is due to a lack of stability from the ZnO nanowires to elevated temperatures. Samples annealed under a constant flow of Argon also exhibit a porous appearance that was not existent on the as-grown nanowires. This phenomenon has been observed in literature and known as Kirkendall's effect owing to a vacancy diffusion mechanism. It is well-accepted that diffusion could occur by direct atomic exchange mechanism, in which atoms migrate by switching positions with atoms on adjacent lattice sites or, another possibility involves lattice vacancies, where an atom moves into a vacant lattice site switching places. As a result, from this effect, the presence of pores is stated in the material formed during diffusion. When the vacancies are substantial to stability in a material, they can expand to restore equilibrium creating pores on the material.

FIG. 4b shows the normalized XRD analysis of the samples under different annealing temperatures under a constant argon flow, the wurtzite structure of ZnO is preserved after annealing. FIGS. 4c and d show a normalized PL spectra regarding the UV peak in order to compare visible light photoluminescence behaviour when annealing the samples. Their area ratio for visible peak over UV peak is then calculated for analysis. The ZnO PL spectra shows a dominant orange emission centred at 610 nm, and a weak UV emission at 380 nm was observed upon excited by light with a wavelength of 300 nm for as deposited sample. When the sample is annealed this UV emission is then increased, therefore the ratio in FIG. 4d from the two peaks always decreases with air annealing. This trend is observed for temperatures up to 400° C., when the porosity appears and in this case, the area-under-the-peak ratio increases considerably in comparison with the previous annealing and the lower temperatures. The extended amount of oxygen vacancies originating the existence of pores due to the Kirkendall effect exhibits a considerably increase of defects in the ZnO nanowires, resulting in the visible peak which reveals the behaviour of defects, explaining why this ratio is increased.

$H_2N_2$ Annealed ZnO Nanowires

Figure 5:
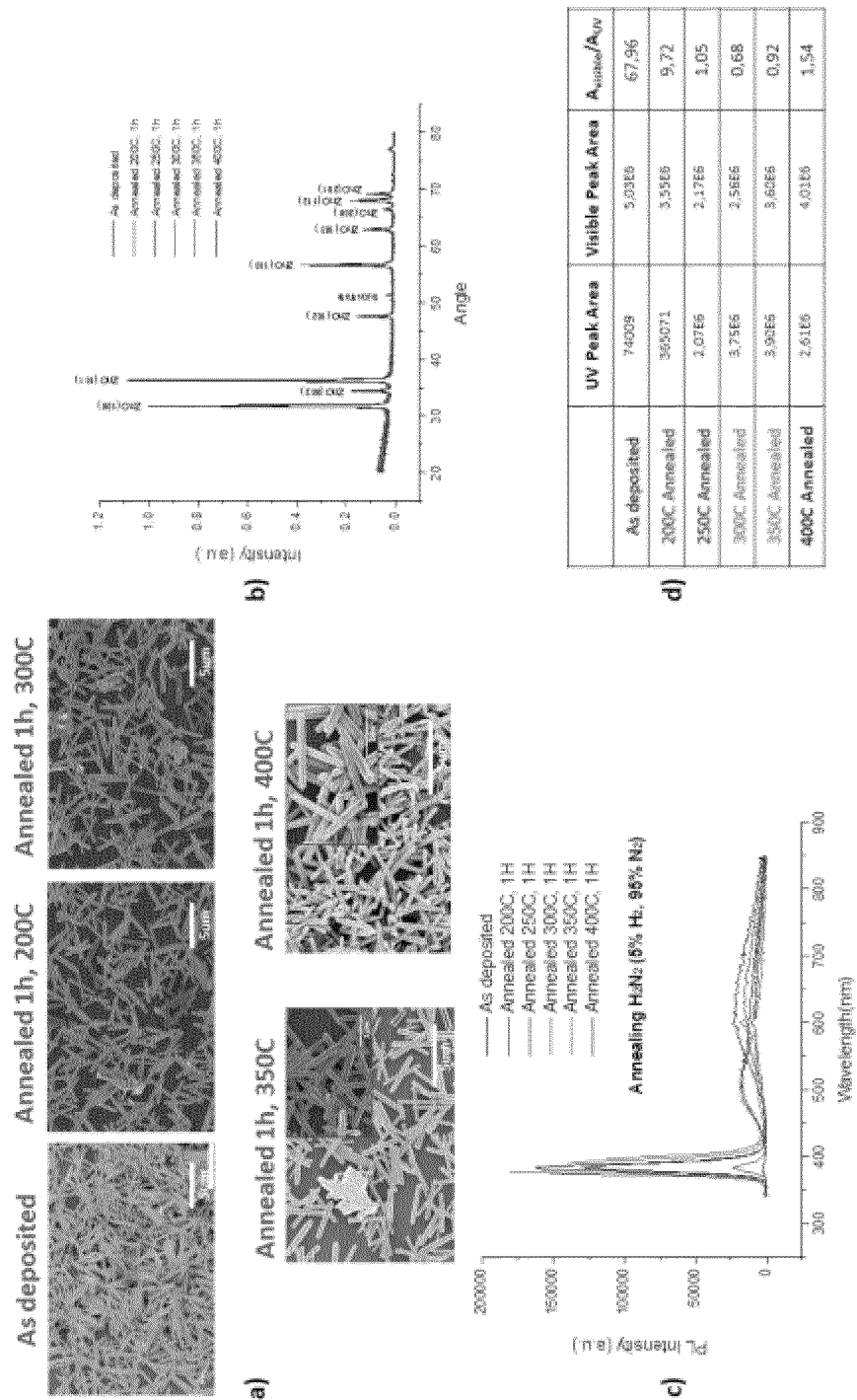
FIG. 5 shows characteristics of $H_2N_2$ annealed ZnO nanowires, according to various embodiments of the invention.

Samples were annealed under a gas composed of 5% Hydrogen and 95% Nitrogen during one hour for different temperatures. The results are reported on FIG. 5. FIG. 5a shows the SEM images of ZnO nanowires for as-grown nanowires, annealed 1 h at 200° C., 300° C., 350° C. and 400° C. The increasing of the annealing temperature is with the purpose of conductivity improvement, when an improvement is no longer observed for $H_2N_2$, the temperature is no longer studied; in the case of air, an improvement was observed up to 350° C. annealing afterwards, the conductivity was no further enhanced. From the SEM pictures, no change is observed at 100° C. as compared to the non-treated sample, when the temperature is increased further than 100° C. under $H_2N_2$ the peeling behaviour already discussed and seen for annealed samples under air and Ar was again observed, once again conforming that the peeling could be due to a lack of stability from the ZnO nanowires to elevated temperatures. Samples annealed under a $H_2N_2$ atmosphere also exhibit a porous appearance as the samples annealed in Ar atmosphere, from SEM images it is observed that the porosity is different. Pores are not uniformed and round-shaped. Nonetheless, once the temperature or the concentration of hydrogen are increased, pores are no longer observed but completely reduced nanowires, result that was not encountered when annealing ZnO nanowires at higher temperatures where the nanowires were porous as the once shown in FIG. 4. Therefore, the porosity presents under $H_2N_2$, besides Kirkendall's effect, is due to the beginning of deterioration of ZnO nanowires. FIG. 5b shows the normalized XRD analysis of the samples under different annealing temperatures under $H_2N_2$ gas, the wurtzite structure of ZnO is preserved after annealing. FIGS. 5c and 5d show a normalized PL spectra regarding the UV peak in order to compare visible light photoluminescence behaviour when annealing the samples. Their area ratio for visible peak over UV peak this then calculated for analysis. The ZnO PL spectra show an orange emission centred at 610 nm for as deposited, 200° C. and 300° C. annealed samples and green emission centered at 520 nm for samples annealed at higher temperatures; and a UV emission at 380 nm was observed upon excited by light with a wavelength of 300 nm. When the sample is annealed, the UV emission is increased, therefore the ratio in FIG. 5d from the two peaks decreases with $H_2N_2$ annealing at 200° C. and 300° C. This trend is observed for temperatures up to 300° C., when green emission is then detected, previous studies on ZnO reported a luminescence green peak at 520 nm, which has been attributed to defects associated with oxygen deficiency. Since orange emission is not completely well-understood but it is well-accepted to agree that interstitials defects play a big role in this emission. Samples annealed a lower temperature under $H_2N_2$ conditions decrease orange-related visible emission related to interstitials and vacancies. The presence of a new peak centered at 520 nm appearing when samples are annealed at higher temperatures, is explained by the creation of oxygen vacancies on ZnO nanowires. The Kirkendall's effect pore creation could be also the reason why nanowires are destroyed after a long exposure to $H_2N_2$ concentrations or even higher temperatures by the expansion of these pores. Furthermore, this could also help the understanding why the area-under-the-peak increases for temperatures above 300° C. since new defects (oxygen vacancies) could be created.

Analysis of the Gas Sensor Properties

For the following tests the substrate that is used comprises a wafer and a $SiO_2$ layer. The $SiO_2$ layer has a thickness equals to 270 nm. The wafer is a silicone substrate wafer having a resistivity comprised between 10 and 20 mOhm.cm and with a p-type (boron) doping. Interdigitated electrodes in gold are used, each having a width of 300 µm. The gap between the electrodes is of 20 µm.

The sensitivity of the Gas Sensor to $O_2$ is Tested

Figure 6:
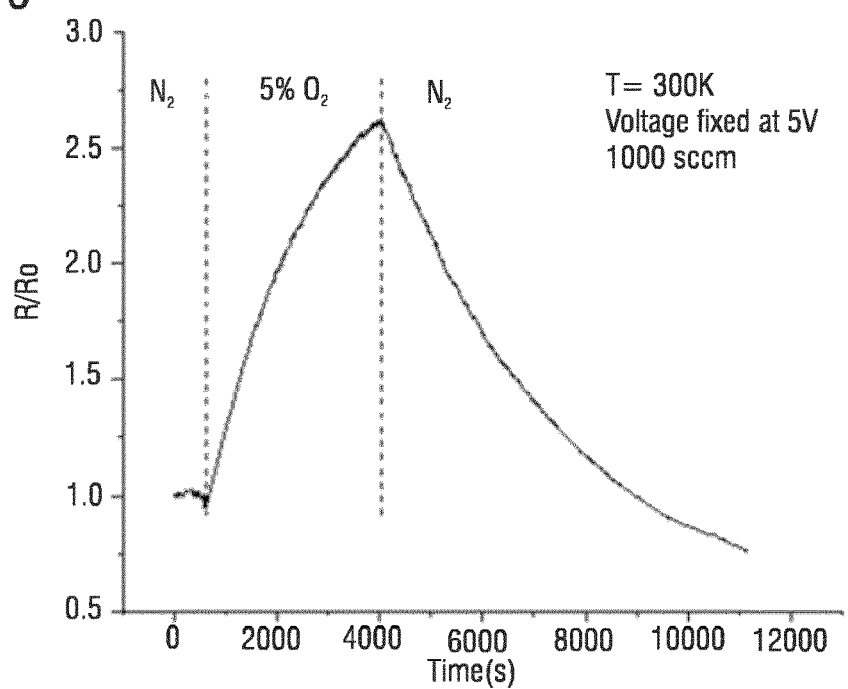
FIG. 6 shows the response of the gas sensor to 5% of oxygen at a fixed bias and at atmospheric pressure, according to various embodiments of the invention.

FIG. 6 shows the response of the gas sensor device of the invention to 5% of oxygen at a fixed bias and at atmospheric pressure. The gas sensor was left under 100% nitrogen during 100 s in order to stabilize the response of the device. The device was then exposed to oxygen during one hour. After exposition to oxygen, the sensor was placed under 100% nitrogen which allows the desorption of the adsorbed oxygen resulting in a resistance decrease. The measurements were performed under a fixed bias at 5 V and at room temperature (300 K). The response to the gas is defined as the relative resistance ratio to the one under neutral conditions such as room temperature under nitrogen gas (Ro) and when exposed to the gas to test (Rg).

Figure 7:
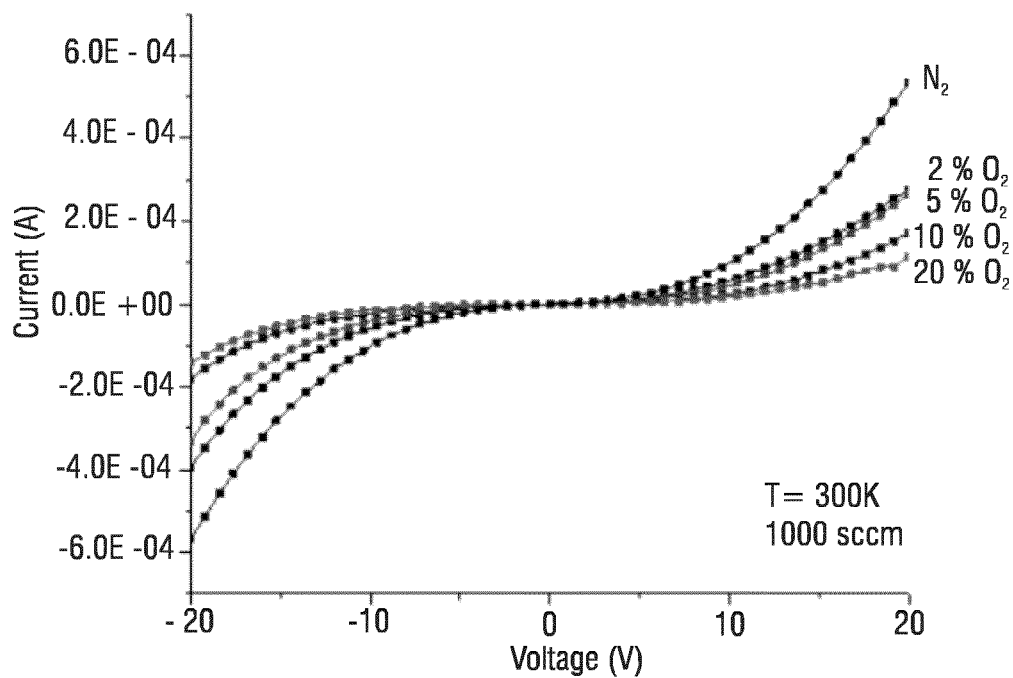
FIG. 7 shows the I-V characteristics of the gas sensor reaction to different concentrations of oxygen, according to various embodiments of the invention.

The recovery of the gas sensor or device due to oxygen desorption takes at least twice the time response to recover and reach its initial state. The results show a high sensibility of the device to gas oxygen at room temperature. clp
Influence of oxygen concentration FIG. 7 shows I-V characteristics of the gas sensor reaction to different concentrations of oxygen at room temperature. The results show that the sensibility of the gas sensor to oxygen increases when the concentration of oxygen increases, even at room temperature. The sensor resistance increases with oxygen compared to an exposition under 100% nitrogen.

Figure 8:
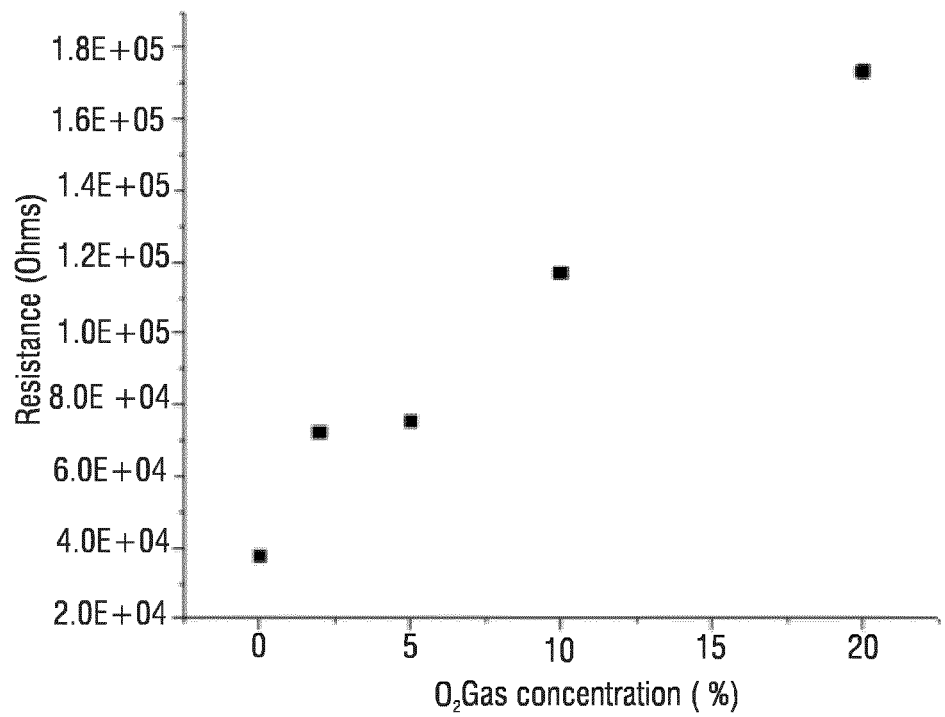
FIG. 8 illustrates the variation of the resistance of the gas sensor of the invention in accordance with oxygen gas concentration, according to various embodiments of the invention.

The variation of the resistance of the gas sensor under the same condition show that the resistance of the device decreases when exposed to lower concentration of oxygen (FIG. 8). These results follow the typical response of ZnO exposed to oxygen.

Influence of Temperature

Figure 9:
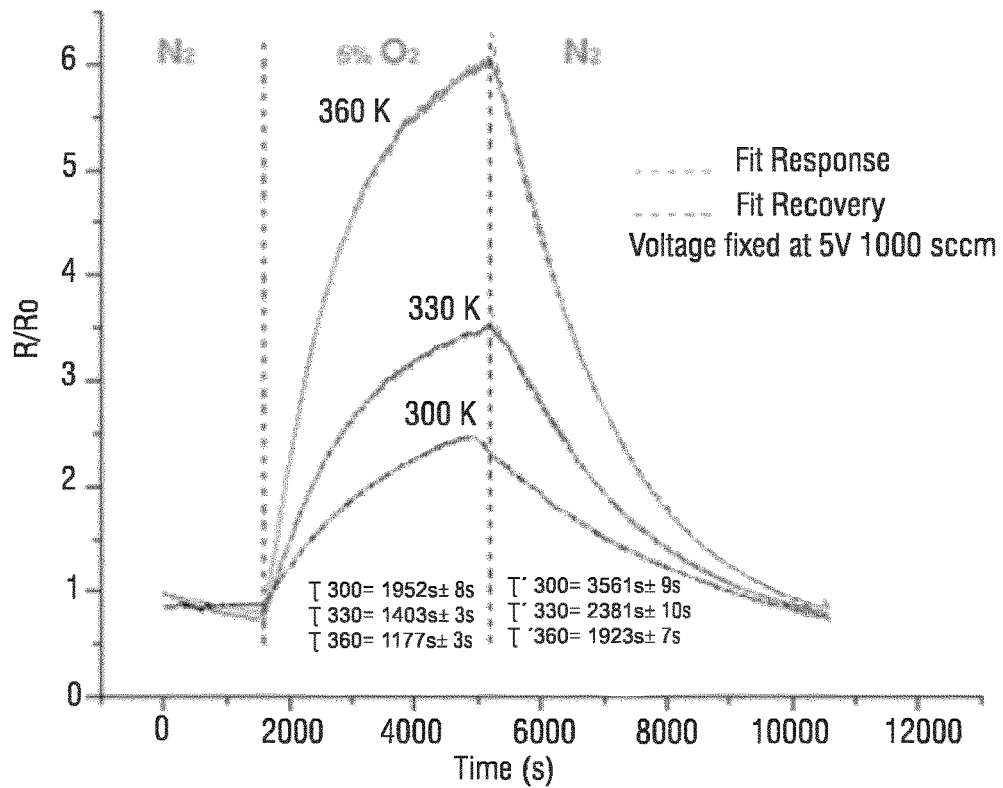
FIG. 9 shows the evolution of the response of the gas sensor of the invention to 5% concentration of oxygen for different temperatures at a fixed bias voltage 5V, according to various embodiments of the invention.
Figure 10:
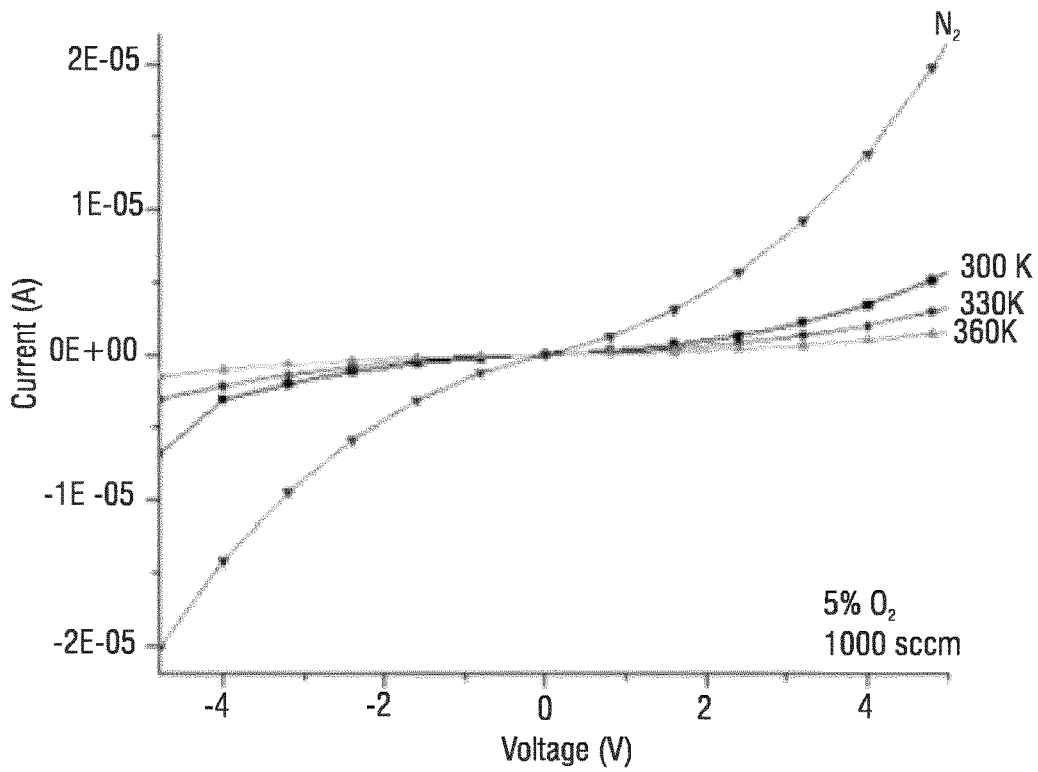
FIG. 10 shows the I-V characteristics of the gas sensor reaction to different temperatures for 5% oxygen concentration, according to various embodiments of the invention.

FIG. 9 shows the evolution of the response of the device of the invention to 5% concentration of oxygen for different temperatures at a fixed bias voltage 5 V. The response characteristics times (τ) are 1952 s, 1403 s, 1177 s for temperatures 300 K, 330 K, 360 K, respectively and the recovery characteristics time (τ') are 3561 s, 2381 s and 1923 s for temperatures 300 K, 330 K and 360 K respectively. The results show that the response increase with high temperatures and thus the resistance increases with the operating temperatures FIG. 10 shows a I-V characteristic of the gas sensor to different reaction temperatures for 5% oxygen. FIG. 10 exhibits a curve. The response increases as function of the temperature and thus the resistance increases with the temperature.

Figure 11:
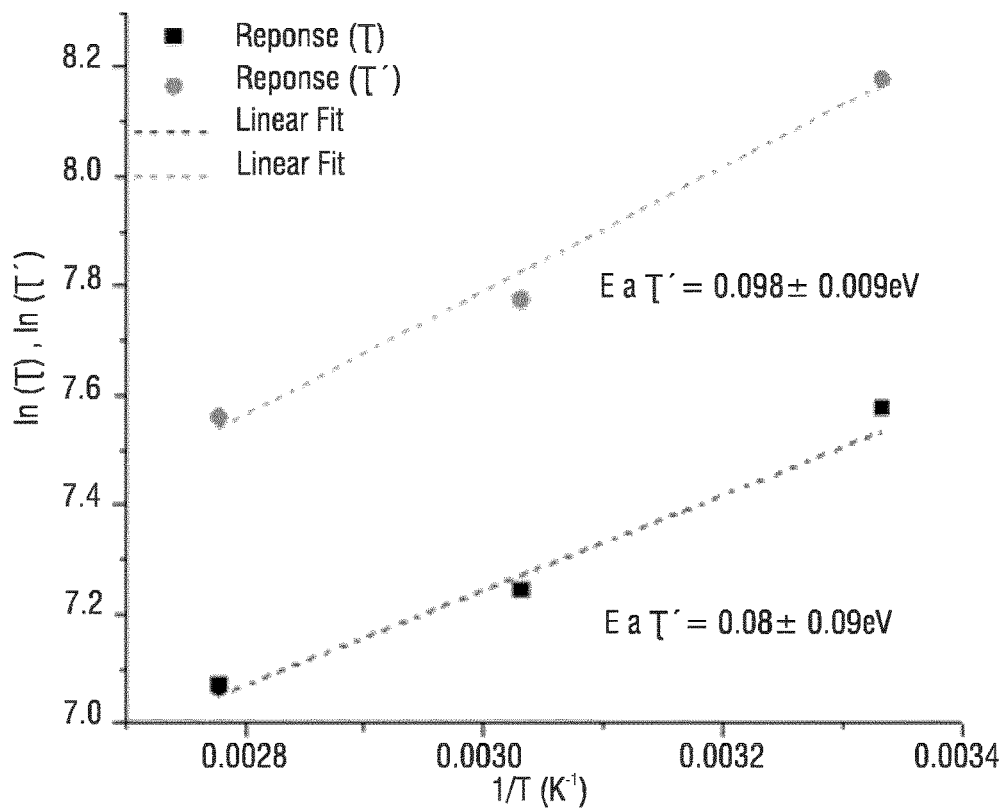
FIG. 11 shows the Arrhenius plot of dynamic sensing characteristics of the gas sensor of the invention at 5% concentration of oxygen for different temperatures, according to various embodiments of the invention.

FIG. 11 shows the Arrhenius plot of dynamics characteristics of the gas sensor under 5% concentration oxygen for different temperatures. The activation energy is determined from slope=Ea/$K_B$ of the graph of FIG. 11. The activation energy of the response to oxygen of the device is 0.08 eV and the activation energy to recover from oxygen is 0.098 eV. The low activation energy obtained for the ZnO nanowires oxidation is smaller than most activation energy values for ZnO structures to be between 0.6 and 5 eV. This result explains the good sensitivity of the gas sensor at low temperature such as room temperature.

Influence of Annealing Atmosphere

Three other different gas sensors have been fabricated and tested: air annealed, argon annealed and $H_2N_2$ (5% $H_2$ and 95% $N_2$) annealed to be compared to the as grown nanowires device sensing mechanism. These sensors are based on nanowires based network with different annealing atmospheres performed at 250° C. during one hour as previously described.

Figure 12:
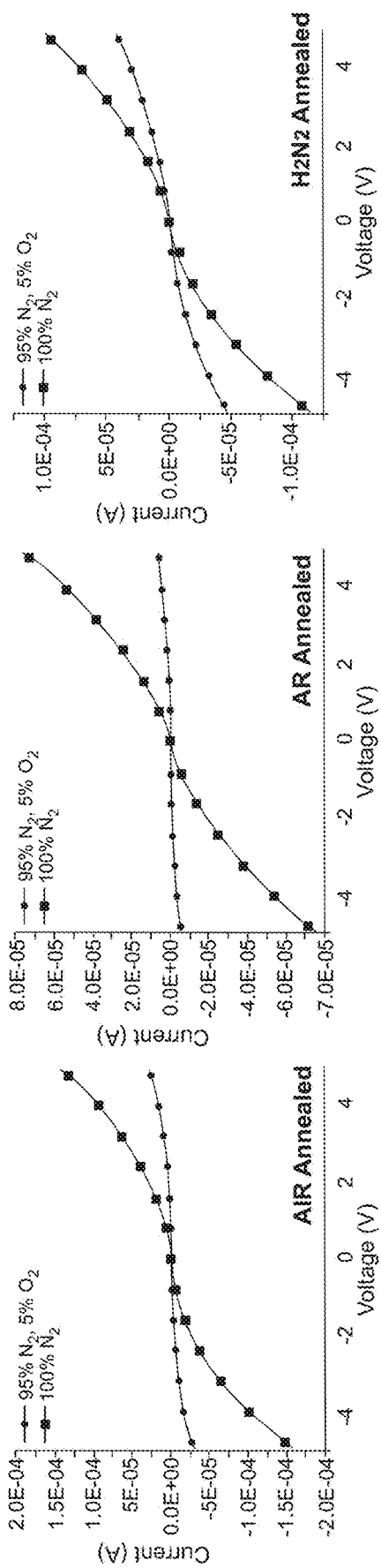
FIG. 12 shows the I-V characteristics of gas sensors for 5% oxygen concentration under annealing conditions, according to various embodiments of the invention.

FIG. 12 shows the I-V characteristics of the three different sensors to 5% Oxygen at atmospheric pressure after one hour. Since the analysed samples contain different treated nanowires and nanowire-network base thin film cannot be guaranteed equal in all samples, a precise comparison cannot be made. In order to estimate different treatments and their influence on the sensing mechanism at different temperatures, the ratio between the sample at 5 V under 100% Nitrogen and when is exposed to 5% Oxygen is calculated. The ratio for the as deposited, air annealed sample, Ar annealed sample and $H_2N_2$ are 3.71, 4.97, 11.89 and 2.22, respectively. This ratio is a factor that indicates the influence of oxygen gas molecules on each sample at 300 K. This factor is higher for argon and air annealed samples but smaller for $H_2N_2$ annealed sample as compared to the as deposited nanowires. An explanation for the results observed in FIGS. 10, 12 and the obtained ratios could be the desorption of organic residues (HMTA, $NH_3$, $NH_x$, and/or NH4+) on nanowires network junctions of the annealed samples, which describe a better response than as deposited sample. Argon annealed sample shows the highest ratio which could imply the formation of defects such as oxygen vacancies that will increase the sensing response to oxygen gas, which could be interpreted by the PL characterization for argon annealed sample at 400° C. previously described. Nevertheless, $H_2N_2$ may release the organic residues (HMTA, $NH_3$, $NH_x$,and/or $NH4^+$) attached to the ZnO nanowires surface but since the response is decreased, and based on the results previously described (Annealing under $H_2N_2$) from where there is a degradation at higher temperatures by Kirkendall's effect. Thus, the nanowire-based thin film could be already degraded which could decrease the sensing response to oxygen gas molecules.

The Sensitivity of the Gas Sensor to $CO_2$ is Tested

Figure 13:
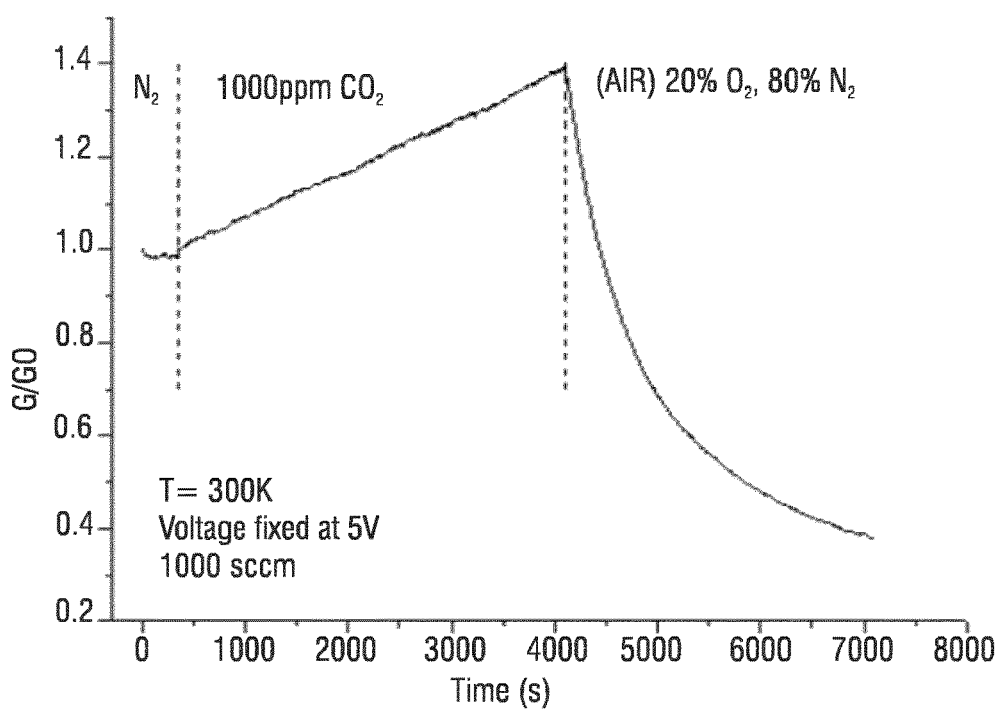
FIG. 13 shows the dynamic sensing characteristic of the gas sensor of the invention exposed at 1000 pm concentration of $CO_2$ at room temperature and at a fixed voltage 5V, according to various embodiments of the invention.

The response to 1000 ppm concentration $CO_2$ was recorded as function of the time and the results are shown on FIG. 13. The sensor was left under 100% nitrogen during 600 s to stabilize the response and was then exposed to 1000 ppm $CO_2$ during one hour. After exposition to $CO_2$, the gas sensor is left under air which is defined as 80% nitrogen and 20% oxygen. The measurements are performed under a fixed bias at 5 V. The results show a good sensibility of the gas sensor to $CO_2$ at room temperature (300 K).

Influence of $CO_2$ Concentration

Figure 14:
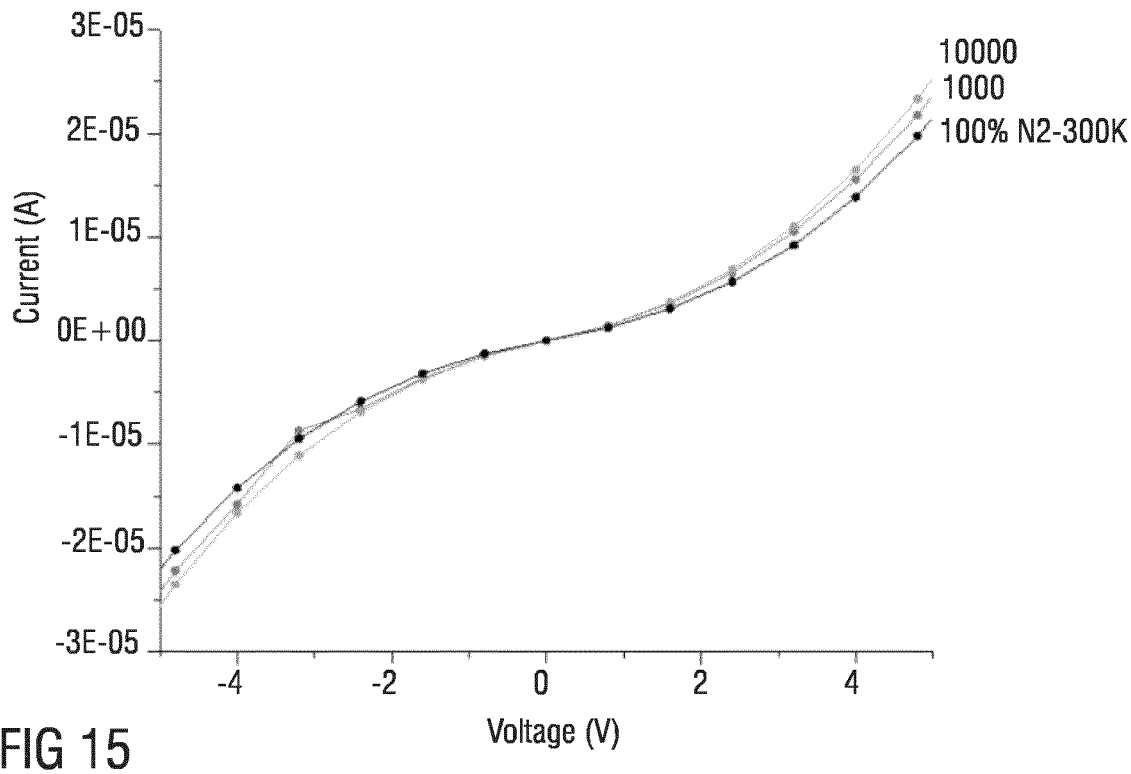
FIG. 14 illustrates the I-V characteristics of the gas sensor of the invention to different concentrations of $CO_2$ at room temperature, according to various embodiments of the invention.

I-V characteristics of the gas sensor have been studied for different concentrations of $CO_2$ molecules at room temperature (300 K). The results are represented on FIG. 14. The resistance decreases when the sensor is exposed to $CO_2$ molecules. The resistance increases when the sensor is exposed to lower concentration of $CO_2$ molecules.

Influence of Temperature

The influence of the temperature on the gas sensor sensitivity has been studied as previously, at atmospheric pressure. The results are shown on FIG. 15. The response characteristic times ($\tau$) of the sensor of the invention are 12002 s, 4867 s and 2540 s for temperatures 300 K, 330 K and 360 K respectively. The recovery characteristics times ($\tau'$) are 813 s, 535 s, 446 s for temperatures 300 K, 330 K, 360 K respectively. The response and recovery times decrease when the temperatures increase The $CO_2$ detection is thus improved when the temperature increases.

Figure 16:
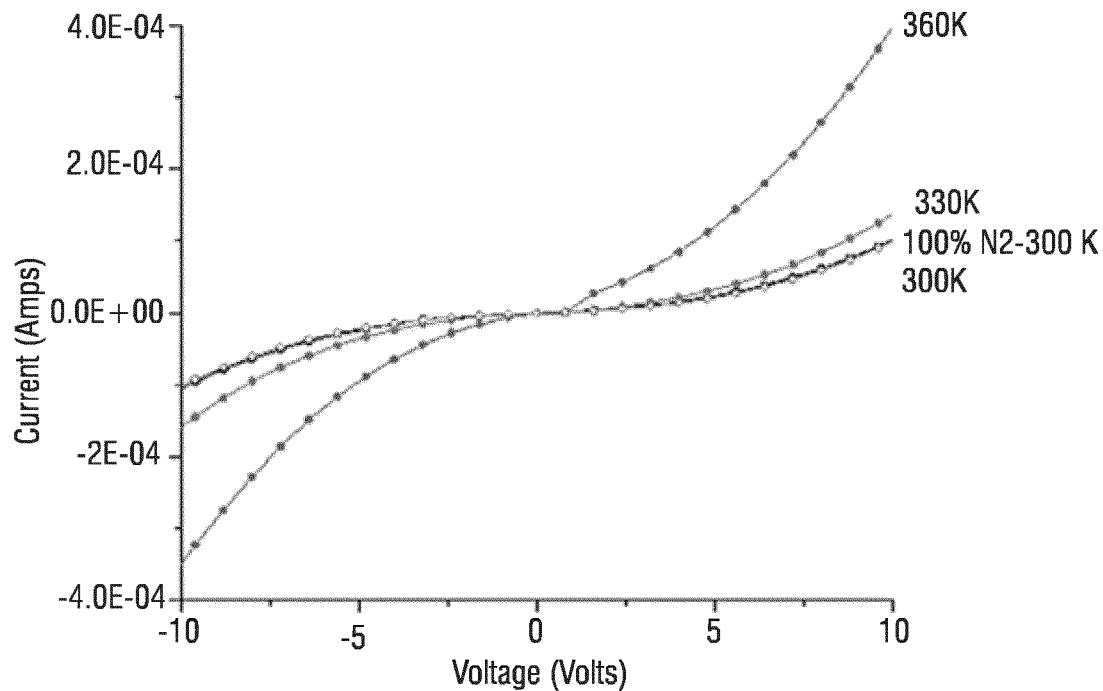
FIG. 16 shows the I-V characteristics of the gas sensor of the invention exposed at 1000 ppm concentration of $CO_2$ at different temperatures, according to various embodiments of the invention.

FIG. 16 shows I-V characteristics of the gas sensor to different temperatures for 1000 ppm $CO_2$ molecules. A major resistance decreases once the temperature increases is observed. At a low operating temperature, the response of the films to $CO_2$ is restricted by the speed of the chemical reaction because the gas molecules do not have enough thermal energy to react with the surface adsorbed oxygen species.

Figure 17:
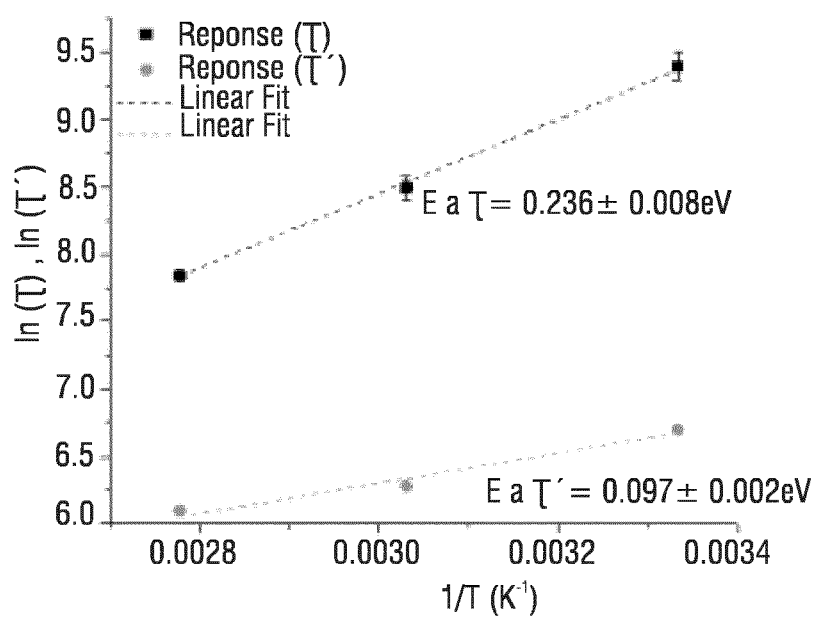
FIG. 17 shows the Arrhenius plot of dynamic sensing characteristics of the gas sensor of the invention under 1000 ppm of $CO_2$ for different temperatures, according to various embodiments of the invention.

FIG. 17 shows an Arrhenius plot based on the values obtained during the dynamic sensing while exposing the gas sensor to $CO_2$. The activation energy of the response of the sensor to $CO_2$ is 0.236 eV and the activation energy to recover from $CO_2$, under 20% oxygen, is 0.097 eV. The activation energy is determined from slope=$Ea/K_B$ of the graph of FIG. 117. The activation energy reported in the literature are comprised between 0.9 and 2 eV. The activation energy of the device is thus lower than those reported in the literature. The difference between the energy of activation to recover from the response could explain the longer reaction time towards $CO_2$ in comparison to oxygen gas.

Influence of Annealing Atmosphere

Figure 18:
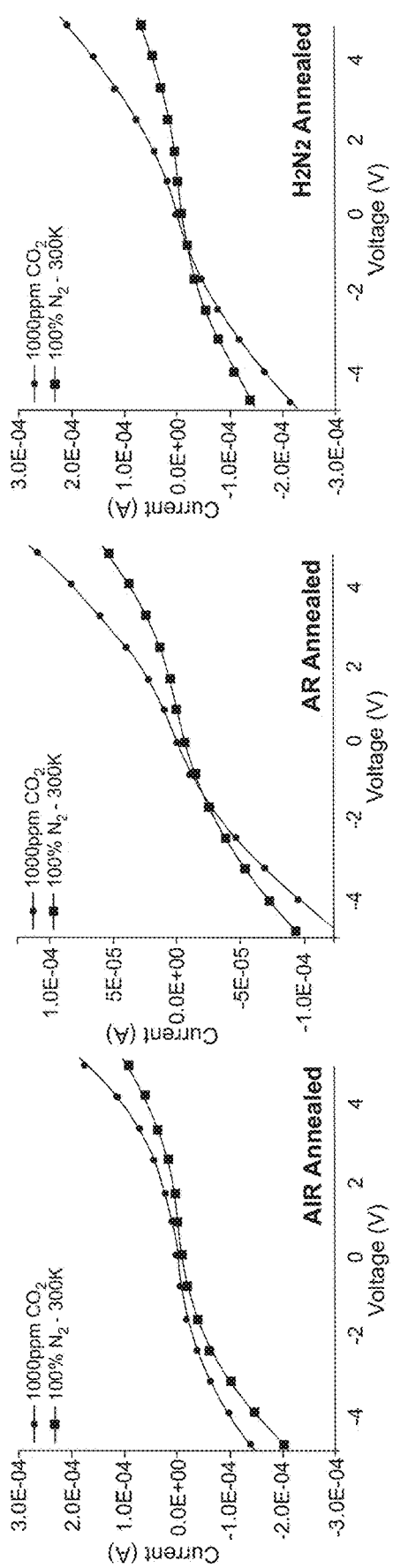
FIG. 18 shows the I-V characteristics of gas sensors exposed to 1000 ppm of $CO_2$ under annealing conditions, according to various embodiments of the invention.

The same study under oxygen gas molecules is now performed under 1000 ppm of $CO_2$ to analyse the influence of defects on the sensing mechanism ZnO nanowire. FIG. 18 shows the I-V characteristics of the three different sensors to 1000 ppm of CO2 at atmospheric pressure after one hour. Since $CO_2$ is a reducing gas, the ratio of the current measured once exposed to $CO_2$ over the initial measured value at 5 V is then considered. The ratio for the as deposited, air annealed sample, Ar annealed sample and $H_2N_2$ are 5.17, 1.8, 2.04 and 2.82, respectively. This ratio is a factor that indicates how the resistance decreases once exposed to $CO_2$ gas molecules at 300 K, the factor of the three anneal samples are smaller than the as deposited nanowires, indicating this one is more suitable to be used as a $CO_2$ sensor.

Electrical Transport Analysis

Two semiconducting interfaces in contact by a junction would have either an Ohmic or Schottky behaviour when a voltage is applied. It is mostly accepted that the non-linear I-V characteristics are strongly attribute to the microstructure composed of n-type semiconducting ZnO grains of the nanowires, and therefore, creates a Schottky contact.

Based on what is proposed in the state-of-the-art for non-linear granular thin films it is proposed a conductive model for ZnO nanowires network-based electrical transport using the method of the invention, where the conductivity is controlled by the potential barriers (grain-to-grain boundaries) and its exponential behaviour as a function of the barrier height. In this manner, the junction properties of ZnO nanowires films and their resistance have been studied in order to draw conclusions about the ZnO network optimization of the gas sensor and its performance obtained with the method of the invention.

Kirchoff law is applied: $U = N_g|_b U_{gb} + R_s I$ (1), where U is total voltage, indicating the conduction is driven by the number of nanowires junctions ($N_{gb}$) on the nanowire-based thin film and the series resistance (Rs) of itself which includes the contact resistance and the nanowire resistance contribution.

Fitting

Figure 19:
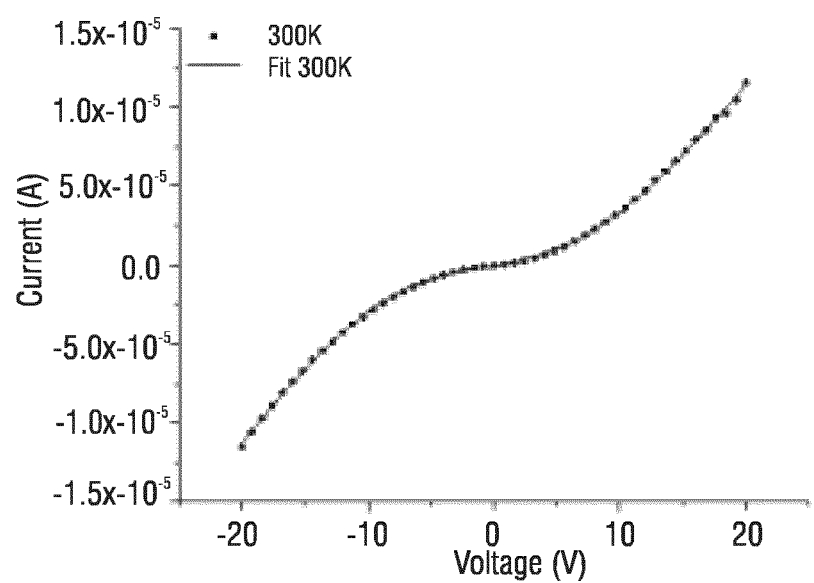
FIG. 19 represents the I-V characteristics of the gas sensor measured in vacuum at room temperature, according to various embodiments of the invention.

FIG. 19 represents the I-V characteristics of the ZnO network of the gas sensor measured in vacuum at room temperature which were fit to the relation for thermionic emission over a barrier (relation below), the two terms of this equation correspond to the two-sided junction (negative and positive voltages) to simulate a symmetric junction.

$$I(U) = I_1 \left( e^{\frac{q(U-IR_S)}{n_1 N_{1,gb} K_B T}} - 1 \right) - I_2 \left( e^{-\frac{q(U-IR_S)}{n_2 N_{2,gb} K_B T}} - 1 \right) \quad (2)$$

$$\text{where } I_{1,2} = AT^2 e^{-\frac{\varphi_b}{K_B T}} \quad (3)$$

$I_{1,2}$ is the amplitude of the current dependent of the Richardson constant from ZnO and the effective area of the junction-based thin film, n is the ideality factor that is a quantity for describing the deviation of the diode from an ideal Schottky barrier, for which n=1, K the Boltzmann constant, T the absolute temperature, q is the charge which dominates the conduction (electrons), $\varphi_B$ the grain boundary potential barrier and, I and V the current measured and applied voltage. It is widely known in literature that one side of equation (2) is solved using LambertW function as follows:

$$I(U) = \frac{nN_{gb}K_B}{qR_S} lambertW \left( \frac{qI_{1,2}R_s}{nN_{gb}K_B} e^{\frac{q(U+I_{1,2}R_S)}{nN_{gb}K_B}} \right) \quad (4)$$

Equation (3) gives a non-linear dependence between I and V, for a given number of junctions on a thin film. This relation will be used as a fit for the collected experimental data of the gas sensor of the invention.

From a first fit, the data appearing in FIG. 19 are fitted using equation (4), this allows to determine the behaviour of some parameters as a function of the pre-determined contact geometries. The following expected hypotheses are described as follows:

a. The number of grain boundaries times the ideality factor will be influenced by the gap in between the electrodes (L), since more junctions will be created, and independent on the contact width (W) of the device as the shortest (horizontal) junctions path is considered to contribute.

b. The series resistance of the device will be dominated by the contact resistance depending inversely with the W and not with L since when larger current is allowed from nanowires junction, the contribution will be reduced. The nanowire resistance itself will be dependent with L and not with W, as only horizontal paths are more likely to contribute in conductivity.

Figure 15:
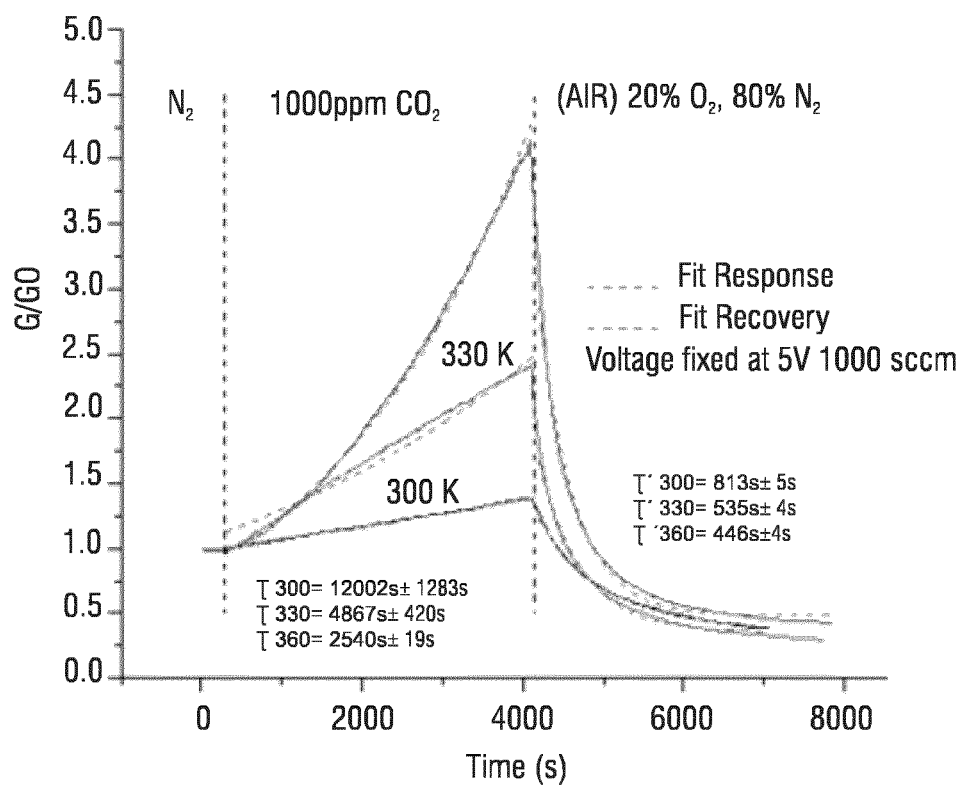
FIG. 15 shows the dynamic sensing characteristics of the gas sensor of the invention exposed at 1000 ppm concentration of $CO_2$ at different temperatures and at fixed voltage 5V, according to various embodiments of the invention.
Figure 20:
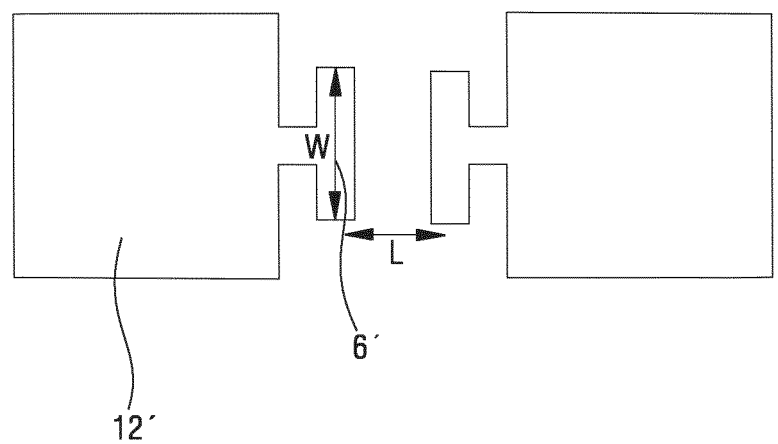
FIG. 20 illustrates squared electrodes, according to various embodiments of the invention.

I-V characteristics of ZnO nanowire network-based sensors were obtained under primary vacuum conditions ($10^{-3}$ mbar) using Cryogenic two probe stations. Squared electrodes are used instead of the previous interdigitated electrodes. The squared electrodes are represented in FIG. 20. The geometries of the electrodes were changed where the gap (L) between the two electrodes varies between 2-20 μm and the electrode width (W) from 10-300 μm. Each electrode 6' is connected to a pad 12' (FIG. 15).

Figure 21:
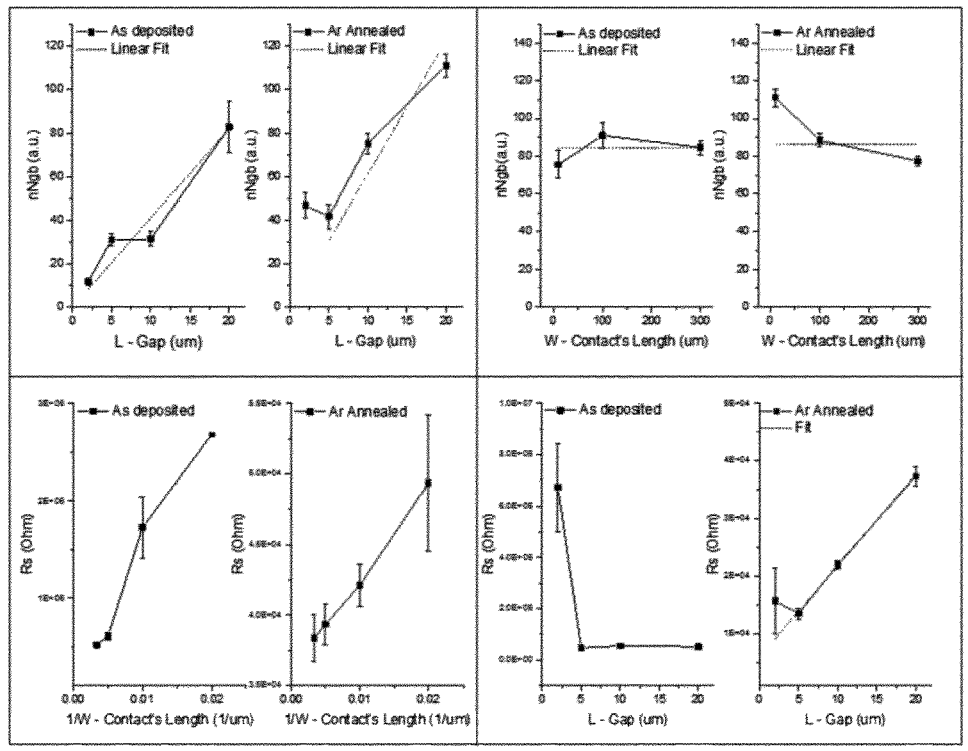
FIG. 21 shows nNgb and Rs parameters behaviour with electrodes geometries (L, W) for samples as deposited (according to the method of the invention) and AR annealed, according to various embodiments of the invention.

The data collected from the different devices was fitted using relation (4) to obtain $nN_{gb}$ and Rs parameters according to electrodes geometries in order to conform the hypothesis explained above. The left and right upper panels from FIG. 16 present the behavior of $nN_{gb}$ of as grown (as deposited by the method of the invention) and argon annealed nanowires with the electrodes geometries L and W. The bottom panels of FIG. 21 exhibit the Rs trend with and without annealing. These behaviours confirm the hypothesis explained above, a linear dependence from the ideality factor times the number of grain boundaries involves in the conduction path to the gap between the electrodes and remaining constant with the electrode width. The series resistance is shown at the FIG. 21 (panel below) conforming its inverse dependence with the electrodes width. Therefore, it can be concluded that the main conductivity contribution comes from created network junctions in which the argon annealed sample improves conductivity by decreasing the contact resistance. This leads the nanowire resistance to appear, showing a linear dependence with L, as it is expected since the number of junctions increases.

For a validation of this model and fitting accuracy, a gas sensor according to the invention having 20 μm gap and 300 μm electrode width is selected due to their maximal junction's contribution between the electrodes's gap and the maximal contact width to enhance current contribution and avoid any noise.

Figure 22:
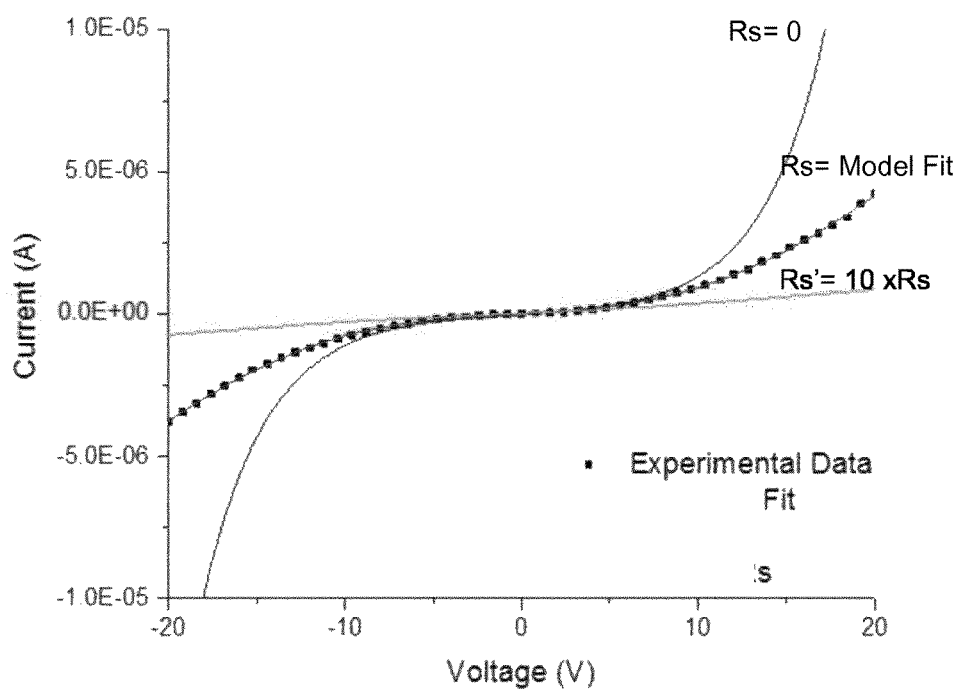
FIG. 22 represents I-V characteristics for ZnO nanowires network-based thin film under vacuum at room temperature, according to various embodiments of the invention.

FIG. 22 presents the obtained experimental data, fitted by using the thermionic emission voltage over a junction relation between the nanowires. As seen before (in FIG. 19), this result reflects a reproducible accurate fitting with the experimental data. In order to validate that the current contribution comes mainly from the nanowires junction, two curves are plotted with the obtained fitting parameters but the series resistance, which is fixed at 0 Ohms (assuming there is no contribution from the nanowire itself or the contact resistance) and, considering the obtained resistance is ten times larger than the value obtained with the fit. When Rs=0 Ohms, the after few volts applied, the current increases exponentially with the voltage as an ideal diode but when the Rs is increased, the amount of current passing through the device is then limited and therefore not exponentially dependant with the voltage. Consequently, from this graph it can be concluded that the conduction mechanism is mainly controlled by the nanowires junctions on the network-based thin film and not by the series resistance coming from the nanowires themselves and the contact resistance.

Influence of Temperature

Figure 23:
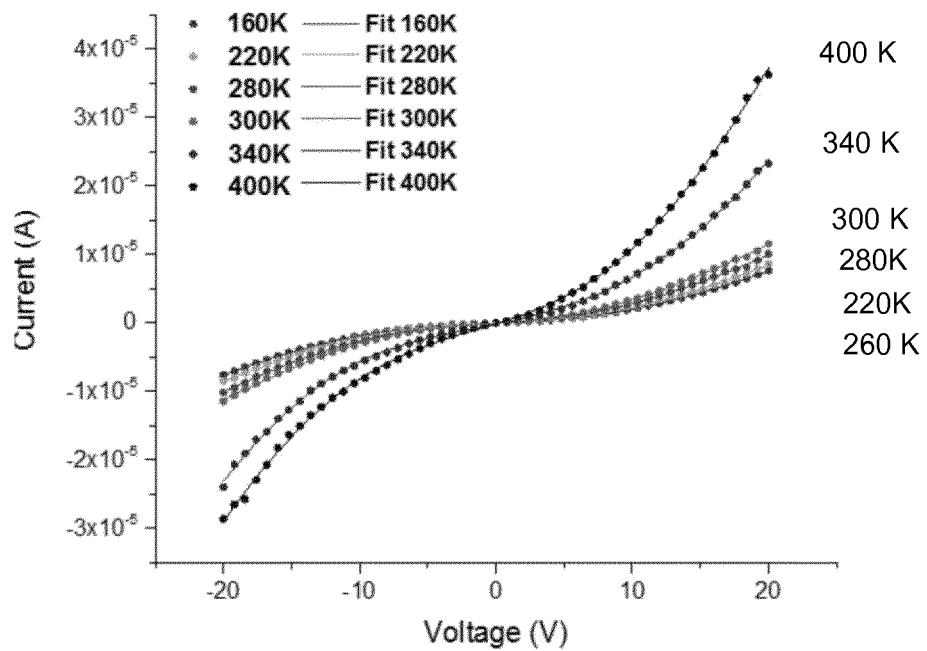
FIG. 23 represents the I-V characteristics measured in vacuum at various temperatures measurements with a non-linear behaviour from −20 V to 20 V, according to various embodiments of the invention.

FIG. 23 presents the I-V characteristics at various temperatures measurements with a non-linear behaviour from −20 V to 20 V. These I-V curves were obtained at 100, 160, 220, 280, 300, 340, and 400 K, respectively. The measured current increases when increasing the temperature from 300 to 400 K, which is commonly accepted for ZnO n-type semiconductor behaviour. The resistivity of the nanowires is thus increased when the temperature decreased from 300 to 100 K, showing a typical semiconductor R vs. T characteristic, which according to thermionic emission induced by the temperature allowing carriers flow over the potential barrier created between the ZnO nanowire-based network film. Since the oxygen vacancies and zinc interstitials are responsible for conductivity in surface, and our ZnO nanowires present high density of these defects it can be concluded that the conductivity contribution may come from surface rather than bulk.

Figure 24:
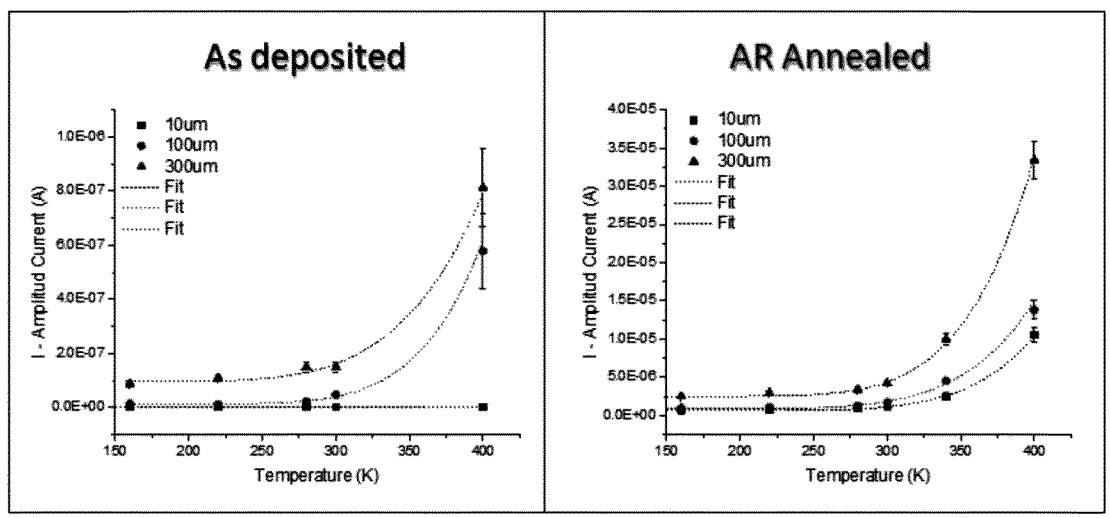
FIG. 24 represent the values $I_1$ and $I_2$ as a function of the temperature for different device geometries, as well as a fit by an exponential law, according to various embodiments of the invention.

From equation (4), the obtained parameter $I_{1,2}$ from this first fit, is then plotted in function of the absolute temperature, revealing a clean exponential dependence behaviour with the temperature (FIG. 24).

From this result, a second fit then realized in order to extract parameters A and $\varphi_B$ (equation (3)) for the different geometries tested. The extracted parameters and the resulting dependence is shown in FIG. 20.

Figure 25:
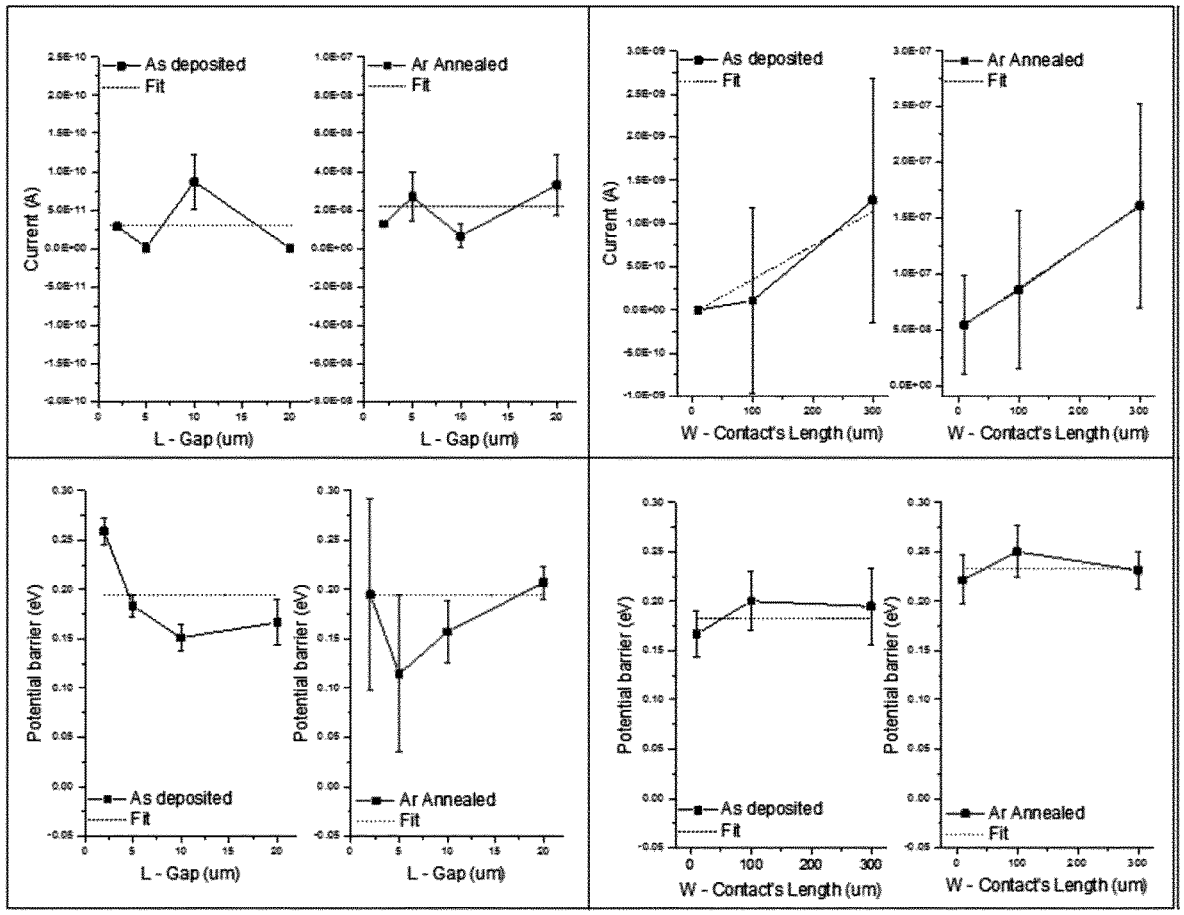
FIG. 25 represents A (current) and $\varphi_B$ (potential barrier) parameters behaviour with contact geometries (L, W), according to various embodiments of the invention.

From FIG. 25, A parameter is completely dependent from W since the current is higher, when the sample is annealed, this contribution is improved, indicating the sample is more conductive. The intersection with y-axis will indicate the leak current for the device, since the conductivity is improved when annealed, this one is as well increased. Leak current for sample as deposited is almost negligible. The potential barrier does not show any dependence neither with L nor with W, meaning the potential barrier ($\varphi_B$) originated from nanowire-to-nanowire junctions boundaries are independent of the contact geometries. Parameters A and φB show higher error bars than the ones in FIG. 21 indicating higher uncertainty. Certainly, when performing a fit it gives an average of the data and therefore is expected to obtain an improvement in terms of accuracy. But, when several parameters are to be determined by a fit, even when accurate, the fact of value compensation from one parameter to another cannot be avoided and thus, a second fit with these parameters, could carry out this compensation effect into a second fit generating more uncertainty. The potential barrier ($\varphi_B$) does not seem to change depending on the surface treatment applied and since the nanowires are the same, the annealing does not change the nature of the junction. Meaning that, the surface treatment applied removes surface contamination or organic residues (HMTA, $NH_3$, $NH_3$, and/or $NH4^+$) on the surface of the ZnO nanowires, increase the doping of native defects such as oxygen vacancies in the surface which originates higher conduction without changing the potential barrier of the nanowire junctions. The obtained values correlate with the accepted values for barrier heights since Au diodes on ZnO can range from 0 to 1.2 eV, depending on the crystal, the surface preparation, and the conditions under which the contact is formed.

Figure 26:
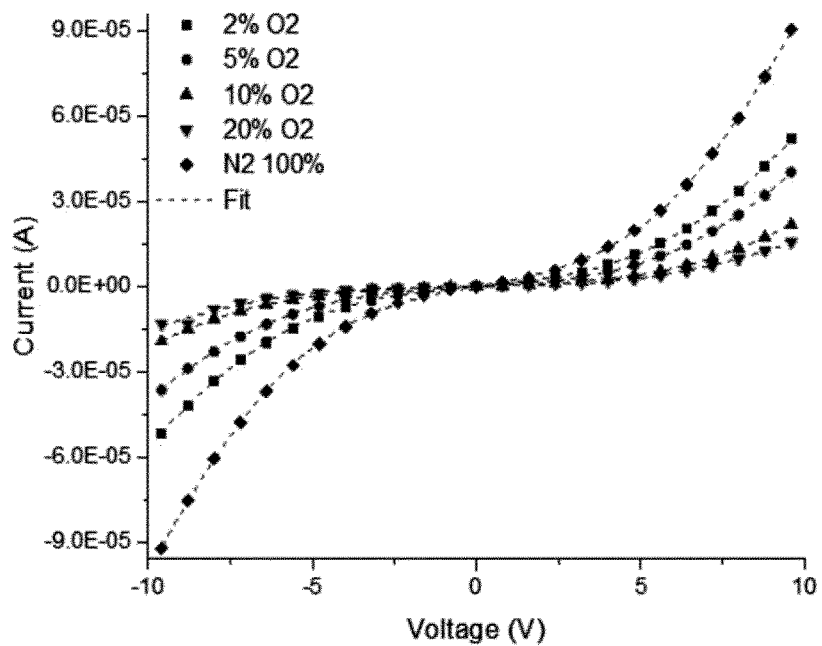
FIG. 26 represents I-V characteristics for ZnO nanowires network-based thin film under varying oxygen concentration from 0 to 20%. The measured device corresponds to L (gap between the electrodes)=20 µm and W (electrodes width)= 300 µm, according to various embodiments of the invention.
Figures 27, 28:
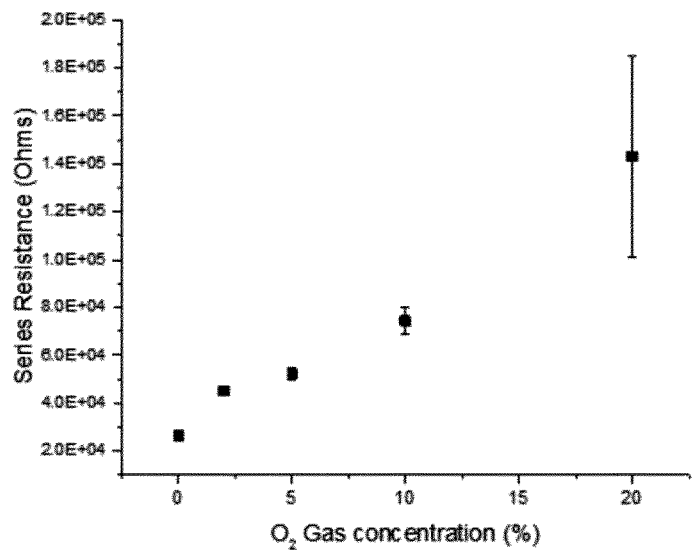
FIG. 27 is a summary table of obtained fit parameters from the I-V characteristics performed in FIG. 25, according to various embodiments of the invention.
FIG. 28 represents the series resistance variation with oxygen gas concentration taken from FIG. 6 calculated from fit parameters, measurements were performed at 300 K, according to various embodiments of the invention.

The electrical transport model of the gas sensor of the invention has been studied. For this analysis, nanowires networks at 300 K under oxygen conditions (since ZnO sensors have shown better response towards oxygen) are considered. FIG. 26 shows the same plot to the oxygen concentration behaviour explained previously in FIG. 14, except that this graph exhibits the fit of the conduction model explained previously. At 300 K, the resistance increases once oxygen molecules are present and when the concentration is increased, the resistance keeps increasing. FIG. 27 summarizes the obtained parameters from fit of curves shown in FIG. 26. From FIG. 27, $V_1$ and $V_2$ remain mostly constant, the series resistance is increased with gas concentration and; parameters $I_1$ and $I_2$ decrease.

Figure 29:
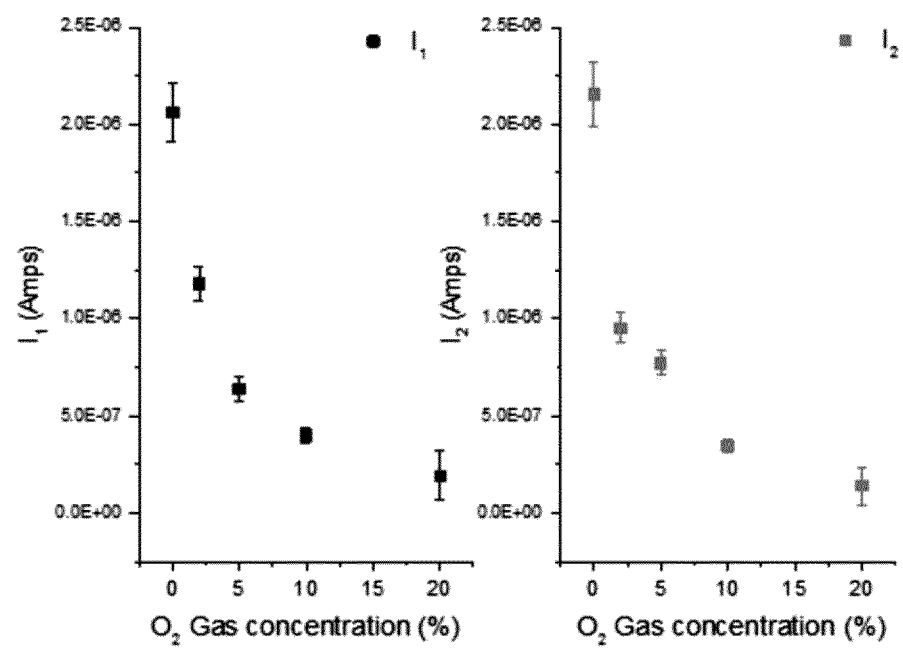
FIG. 29 represents $I_1$ and $I_2$ variation with oxygen gas concentration taken from FIG. 6 calculated from fit parameters, measurements were performed at 300 K, according to various embodiments of the invention.

$V_1$ and $V_2$ are dependent on the number of junctions involved and the ideality factor of the sensing device. From FIG. 27 it can be concluded that the number of nanowire-to-nanowire junctions present in the thin film and their ideality factor n remain constant when exposing to a gas. These results are expected, the number of junctions on the nanowire thin film is a geometrical parameter that is not expected to change in contact with gas. However, recent studies have shown changes on the ideality factor towards different environments or operating temperature. If no change is observed on the ideality factor for this case, this would mean the nature of the ZnO nanowire network-based thin films junctions is remains the same. The series resistance evolution with gas concentration indicated in FIG. 28 is increased once oxygen molecules are exposed and continues to increase with concentration which correlates with previous results and literature-predicted behaviour under oxidant conditions as discussed earlier. This linear dependence, which involves the nanowire surface, towards gas concentration reflects high response and sensitivity to oxygen molecules. Parameters $I_1$ and $I_2$ are plotted in function of the oxygen gas concentration in FIG. 29. $I_1$ and $I_2$ are given by the equation (3) where $K_B$ and T are constants and A depends on the Richardson constant and the working area of the gas sensor, which are geometrical parameters that do not change in presence of gas.

From this equation, it could be concluded that according to $I_1$ and $I_2$ results towards oxygen concentration, the potential barrier behaviour could be predicted from these parameters. $I_1$ and $I_2$ values decrease exponentially when exposing to larger concentration of oxygen molecules, following (3) for $I_1$ and $I_2$ and the potential barrier, leads to the conclusion the potential barrier $_TB$ increases with gas concentration of oxygen. This means oxygen absorbed ZnO nanowires not only reduces the electrons producing conductivity but it affects the junction properties by increasing the junction barrier formed by the nanowire-to-nanowire contact. From this analysis, it is concluded that, the potential barrier which increases with gas concentration dominating the response at very low voltages. At higher voltages, such at 5 V (see FIG. 10), the response mechanism is mainly dominated by the series resistance which, in this case, corresponds to the nanowire resistance.

EXPERIMENTAL PART

Annealing

The samples were annealed at different temperatures for one hour at environmental conditions (air) and under a constant flow of argon using a temperature-controlled stage of Bruker D8 HR X-ray diffractometer. Samples annealed under a reducing gas ($H_2N_2$) were prepared with Annealsys® RTCVD AS-MASTER 2000 using different concentrations of hydrogen. The AS-Master rapid thermal processor allows processes from annealing to Rapid Thermal Chemical Vapor Deposition. Annealing processes can go up to 1450° C. providing a suitable high controlled-process under ultra clean environment. The extended temperature range, the vacuum performance (atmosphere to $10^{-6}$ Torr) and gas mixing capability make reproducible processes.

Scanning Electron Microscopy (SEM)

The morphology of the samples was examined by SEM-FIB (Focused Ion Beam) HeliosNanolab 650 from FEI. The images were recorded with an acceleration voltage of 5 kV and a current intensity of 25 mA.

X-ray Diffraction (XRD)

The diffractometer used is a D8 diffractometer from the Bruker supplier equipped with a copper X-ray source with an emission wavelength of =0.1542 nm. The diffractograms are recorded in ⌊-2θ mode, analysing from 20° to 60°. The samples are carefully placed on the analysis zone by orienting them to avoid the substrate diffraction planes (in this case, silicon substrates).

Photoluminescence (PL)

The photoluminescence (PL) spectra of the adsorbed ZnO nanowires were measured at room temperature and carried out using an Infinite UV-Visible spectrometer M1000 Pro from TECAN®. This spectrometer is equipped with a monochromator allowing the selection of different excitation wavelengths, from the ultraviolet to infrared. Since the ZnO bandgap is 3.37 eV, or around 380 nm, the excitation source is fixed at 300 nm. The spectral range of detection extends from 300 nm up to 800 nm, in order to detect the luminescence due to the excitonic recombination (towards 380 nm) of the ZnO, as well as that due to the recombination of the different levels of transitions induced by defects in the material around 500-600 nm.

Electrical Characterization Cryo

I-V characteristics of the ZnO nanowires were measured using a Field-Upgradeable Cryogenic Probe Station CPX Model from Lake Shore Cryotronics®, Inc. The CPX operates over a temperature range of 4.2 K to 400 K. The probe station provides efficient temperature operation and control with a continuous refrigeration system using nitrogen or helium. A control heater on the sample stage along with the radiation shield heaters provide the probe station with fast thermal response. A Keithley 4200 source measure unit was used to measure resistivity of the nanowires-based network. The barrier height and ideality factor for the deposited film were extracted from the I-V curves. Sensor response and recovery under presence of different gases behaviour was also studied using this equipment which allows to control chamber pressure (kept constant at 1 atm) and gas flow inside the chamber.

The invention claimed is:

1. A method for producing a gas sensor comprising a step of providing a substrate with two coplanar electrodes and a step of forming a ZnO nanowires network on the two coplanar electrodes, wherein the step of forming the ZnO nanowires network on the two coplanar electrodes is performed as follows:
    a) synthesizing ZnO nanowires with a liquid phase sequential growth method;
    b) dispersing the synthesized ZnO nanowires in a solvent to form a solution;
    c) drop casting the solution containing the solvent and the ZnO nanowires on the two coplanar electrodes; and
    d) drying the solution at a temperature inferior to 85° C. without annealing;
    wherein the steps of drop casting and of drying are repeated together at least one time.

2. The method according to claim 1, wherein the step of synthesizing the ZnO nanowires comprises the sub-steps of subsequently:

a) preparing a solution of zinc chloride and hexamethylenetetramine dissolved into water, wherein the zinc chloride and the hexamethylenetetramine are equimolar;

b) heating the solution at a temperature comprised between 70° and 90° C.; and c) adding every 100 minutes, equimolar amounts of zinc chloride and hexamethylenetetramine into the solution while keeping the heating.

3. The method according to claim 2, wherein the sub-step c) is repeated at least one time.

4. The method according to claim 1, wherein the step of synthesizing the ZnO nanowires is performed under stirring.

5. The method according to claim 1, wherein the step of drop casting comprises depositing a droplet of 50 μL of the solution on the two coplanar electrodes.

* * * * *